(12) United States Patent
Bensussan et al.

(10) Patent No.: US 12,319,745 B2
(45) Date of Patent: Jun. 3, 2025

(54) ANTIBODIES HAVING SPECIFICITY FOR CD38 AND USES THEREOF

(71) Applicants: INSERM (INSTITUT NATIONAL DE LA SANTÉ ET DE LA RECHERCHE MÉDICALE), Paris (FR); UNIVERSITÉ DE PARIS, Paris (FR)

(72) Inventors: Armand Bensussan, Paris (FR); Jean-Christophe Bories, Paris (FR); Maxime Fayon, Paris (FR); Carolina Martinez-Cingolani, Paris (FR)

(73) Assignees: INSERM (INSTITUT NATIONAL DE LA SANTE ET DE LA RECHERCHE MEDICALE), Paris (FR); UNIVERSITE DE PARIS, Paris (FR)

( * ) Notice: Subject to any disclaimer, the term of this patent is extended or adjusted under 35 U.S.C. 154(b) by 809 days.

(21) Appl. No.: 17/627,674

(22) PCT Filed: Jul. 15, 2020

(86) PCT No.: PCT/EP2020/070057
§ 371 (c)(1),
(2) Date: Jan. 16, 2022

(87) PCT Pub. No.: WO2021/009263
PCT Pub. Date: Jan. 21, 2021

(65) Prior Publication Data
US 2022/0251234 A1 Aug. 11, 2022

(30) Foreign Application Priority Data
Jul. 16, 2019 (EP) ..................................... 19186591

(51) Int. Cl.
*C07K 16/28* (2006.01)
*A61K 38/00* (2006.01)
(Continued)

(52) U.S. Cl.
CPC .......... *C07K 16/2896* (2013.01); *A61K 40/11* (2025.01); *A61K 40/31* (2025.01);
(Continued)

(58) Field of Classification Search
CPC ............ C07K 16/2896; C07K 16/2809; C07K 2317/24; C07K 2317/31; C07K 2317/565; C07K 2317/622; C07K 2319/02; C07K 2319/03; C07K 2319/30; C07K 2317/56; C07K 2319/00; C07K 2319/33; C07K 16/468; C07K 14/7051; C07K 16/46; A61K 40/11; A61K 40/31; A61K 40/33; A61K 40/4222; A61K 38/00; A61K 2039/505; A61K 2239/31; A61K 2239/38; A61K 2239/48; A61K 39/39541;
(Continued)

(56) References Cited

U.S. PATENT DOCUMENTS

| | | |
|---|---|---|
| 2013/0058921 A1 | 3/2013 | Van Rhee |
| 2017/0166623 A1 | 6/2017 | Theravectys |
| 2019/0135937 A1 | 5/2019 | Zhang et al. |

FOREIGN PATENT DOCUMENTS

| | | | |
|---|---|---|---|
| CN | 107531800 A | 1/2018 | |
| CN | 109734814 A | 5/2019 | |
| CN | 110157679 A | 8/2019 | |
| CN | 111171158 A | 5/2020 | |
| EA | 201991027 A1 | 9/2019 | |
| WO | WO-2015184203 A1 * | 12/2015 | ................ A61P 1/04 |
| WO | 2017025323 A1 | 2/2017 | |

(Continued)

OTHER PUBLICATIONS

Niels W.C.J. Van De Donk et al, "CD38 Antibodies in Multiple Myeloma: Mechanisms of Action and Modes of Resistance", Frontiers in Immunology, vol. 9, Sep. 20, 2018 (Sep. 20, 2018), p. 2, right-hand coumn, paragraph 4—paragraph 5 p. 4, right-hand column, paragraph 2 p. 7, right-hand coumn, paragraph 1—p. 8, left-hand column, paragraph 1.

(Continued)

*Primary Examiner* — Joanne Hama
*Assistant Examiner* — Amy M. Chattin
(74) *Attorney, Agent, or Firm* — WCF IP

(57) ABSTRACT

CD38 is also expressed in a variety of malignant hematological diseases, including multiple myeloma. In the present invention, the inventors have generated a new antibody against CD38 that could be suitable for producing bispecific antibodies as well as CAR-T cells. In particular, the inventors report the development of Bi38-3, a new bispecific T cell engager that targeted CD38 on MM cells and recruited cytotoxic T cells through the CD3ε. Bi38-3 lacked the Fc region of natural mAb, which contributes to resistance processes, but triggered T cells to proliferate, release cytokine and lyse CD38 positive MM cells in vitro. Similarly, Bi38-3 induced autologous T cells to eliminate tumor plasma cells isolated from MM patients both at diagnosis and at relapse. The cytotoxicity triggered by Bi38-3 was restricted to cells expressing high levels of CD38 and preserved the integrity of T, B and NK lymphocytes in vitro. Importantly, Bi38-3 rapidly reduced tumor cells in an MM1.S xenograft mouse model of human MM. Taken together, the results show that the antibody of the present invention is an effective reagent to specifically eliminate CD38 positive malignant cells without significantly affecting CD38 lowly expressing cells and represents a promising novel immunotherapeutic tool for the treatment of malignant hematological diseases, and especially multiple myeloma.

Figure 1:
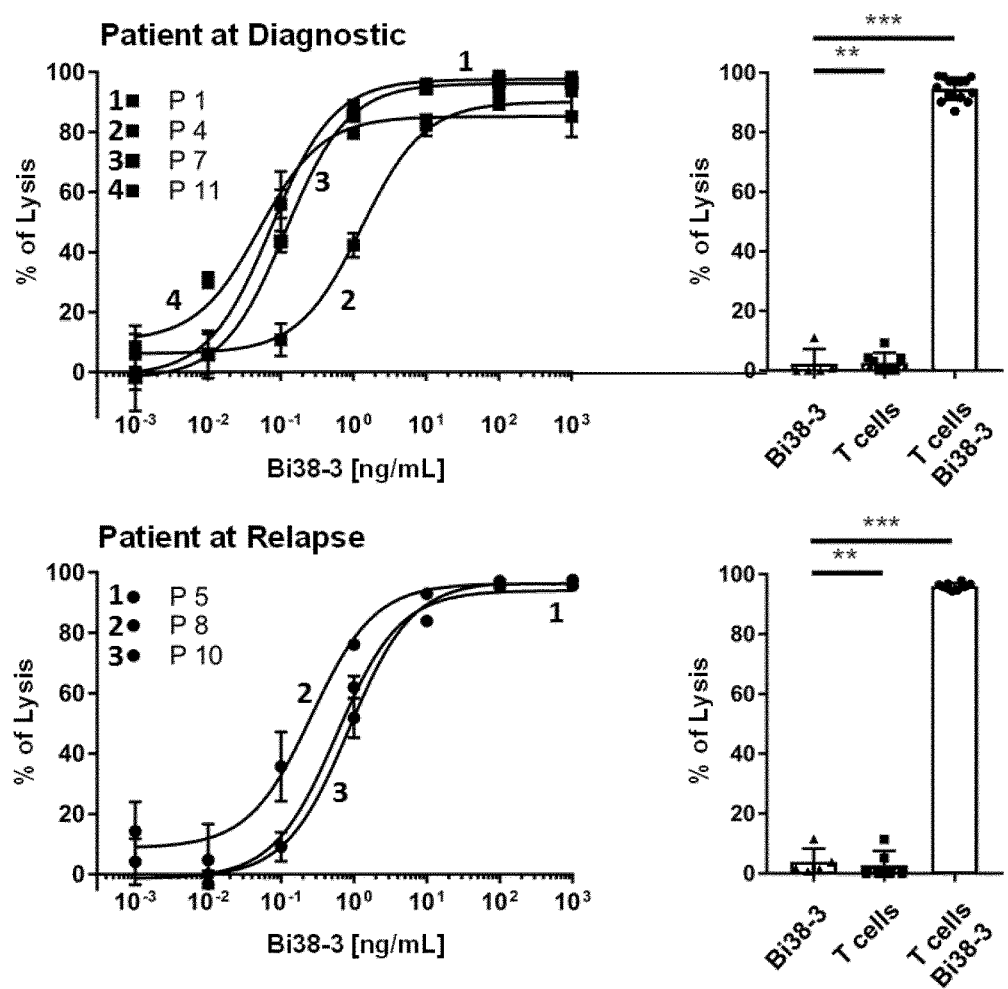

25 Claims, 4 Drawing Sheets
Specification includes a Sequence Listing.

(51) Int. Cl.
  *A61K 39/00* (2006.01)
  *A61K 40/11* (2025.01)
  *A61K 40/31* (2025.01)
  *A61K 40/33* (2025.01)
  *A61K 40/42* (2025.01)
  *A61P 35/00* (2006.01)
  *C12N 5/0783* (2010.01)

(52) U.S. Cl.
  CPC .......... *A61K 40/33* (2025.01); *A61K 40/4222* (2025.01); *A61P 35/00* (2018.01); *C07K 16/2809* (2013.01); *C12N 5/0636* (2013.01); *A61K 38/00* (2013.01); *A61K 2039/505* (2013.01); *A61K 2239/31* (2023.05); *A61K 2239/38* (2023.05); *A61K 2239/48* (2023.05); *C07K 2317/24* (2013.01); *C07K 2317/31* (2013.01); *C07K 2317/565* (2013.01); *C07K 2317/622* (2013.01); *C07K 2319/02* (2013.01); *C07K 2319/03* (2013.01); *C07K 2319/30* (2013.01)

(58) Field of Classification Search
  CPC .......... A61K 39/39558; A61K 39/4631; A61K 39/4611; A61K 39/4633; A61K 39/464426; A61P 35/00; C12N 5/0636; C12N 2510/00
  See application file for complete search history.

(56) References Cited

FOREIGN PATENT DOCUMENTS

| WO | WO-2021009263 A1 | * | 1/2021 | ............. A61K 35/17 |
| WO | WO-2022216723 A1 | * | 10/2022 | ............. A61K 35/17 |
| WO | WO-2024052318 A1 | * | 3/2024 | ......... A61K 39/4611 |

OTHER PUBLICATIONS

Esther Drent, Pre-clinical evaluation of CD38 chimeric antigen receptor engineered T cells for the treatment of multiple myeloma Haematologica. May 2016; 101(5): 616-625.

* cited by examiner

A

B

SEQUENCE LISTING

```
<160> NUMBER OF SEQ ID NOS: 20

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80
```

Asp Cys Gln Ser Val Trp Asp Ala Phe Lys Gly Ala Phe Ile Ser Lys
            85                  90                  95

His Pro Cys Asn Ile Thr Glu Glu Asp Tyr Gln Pro Leu Met Lys Leu
        100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 2
<211> LENGTH: 207
<212> TYPE: PRT
<213> ORGANISM: Homo sapiens

<400> SEQUENCE: 2

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys

```
                  145                 150                 155                 160
            Pro Val Thr Arg Gly Ala Gly Gly Arg Gln Arg Gly Gln Asn
                              165                 170                 175
            Lys Glu Arg Pro Pro Val Pro Asn Pro Asp Tyr Glu Pro Ile Arg
                              180                 185                 190
            Lys Gly Gln Arg Asp Leu Tyr Ser Gly Leu Asn Gln Arg Ile
                              195                 200                 205
```

<210> SEQ ID NO 3
<211> LENGTH: 121
<212> TYPE: PRT
<213> ORGANISM: Mus musculus

<400> SEQUENCE: 3

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
            35                  40                  45

Gly Ala Ile Tyr Pro Gly Asp Gly Asp Thr Arg Tyr Thr Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Asn Leu Thr Ser Glu Asp Ser Ala Val Tyr Tyr Cys
                85                  90                  95

Ala Arg Glu Arg Thr Thr Gly Ala Pro Arg Tyr Phe Asp Val Trp Gly
                100                 105                 110

Ala Gly Thr Thr Val Thr Val Ser Ser
            115                 120
```

<210> SEQ ID NO 4
<211> LENGTH: 107
<212> TYPE: PRT
<213> ORGANISM: Mus musculus

<400> SEQUENCE: 4

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Phe
                20                  25                  30

Leu Ala Trp Tyr Gln Gln Lys Gln Gly Lys Ser Pro Gln Leu Leu Val
            35                  40                  45

Tyr Asn Thr Lys Thr Leu Thr Glu Gly Val Pro Ser Arg Phe Ser Gly
        50                  55                  60

Ser Gly Ser Gly Thr Gln Phe Ser Leu Lys Ile Asn Asn Leu Gln Pro
65                  70                  75                  80

Glu Asp Phe Gly Ser Tyr Tyr Cys Gln His Tyr Gly Ile Pro Leu
                85                  90                  95

Thr Phe Gly Ala Gly Thr Lys Leu Glu Leu Lys
            100                 105
```

<210> SEQ ID NO 5
<211> LENGTH: 8
<212> TYPE: PRT
<213> ORGANISM: Mus musculus

<400> SEQUENCE: 5

```
Gly Tyr Thr Phe Thr Ser Tyr Trp
1               5

<210> SEQ ID NO 6
<211> LENGTH: 8
<212> TYPE: PRT
<213> ORGANISM: Mus musculus

<400> SEQUENCE: 6

Ile Tyr Pro Gly Asp Gly Asp Thr
1               5

<210> SEQ ID NO 7
<211> LENGTH: 14
<212> TYPE: PRT
<213> ORGANISM: Mus musculus

<400> SEQUENCE: 7

Ala Arg Glu Arg Thr Thr Gly Ala Pro Arg Tyr Phe Asp Val
1               5                   10

<210> SEQ ID NO 8
<211> LENGTH: 6
<212> TYPE: PRT
<213> ORGANISM: Mus musculus

<400> SEQUENCE: 8

Glu Asn Ile Tyr Ser Phe
1               5

<210> SEQ ID NO 9
<211> LENGTH: 3
<212> TYPE: PRT
<213> ORGANISM: Mus musculus

<400> SEQUENCE: 9

Asn Thr Lys
1

<210> SEQ ID NO 10
<211> LENGTH: 9
<212> TYPE: PRT
<213> ORGANISM: Mus musculus

<400> SEQUENCE: 10

Gln His His Tyr Gly Ile Pro Leu Thr
1               5

<210> SEQ ID NO 11
<211> LENGTH: 243
<212> TYPE: PRT
<213> ORGANISM: Artificial
<220> FEATURE:
<223> OTHER INFORMATION: Synthetic scFV antibody

<400> SEQUENCE: 11

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Phe
            20                  25                  30

Leu Ala Trp Tyr Gln Gln Lys Gln Gly Lys Ser Pro Gln Leu Leu Val
        35                  40                  45

Tyr Asn Thr Lys Thr Leu Thr Glu Gly Val Pro Ser Arg Phe Ser Gly
```

```
                  50                  55                  60
Ser Gly Ser Gly Thr Gln Phe Ser Leu Lys Ile Asn Asn Leu Gln Pro
 65                  70                  75                  80

Glu Asp Phe Gly Ser Tyr Tyr Cys Gln His His Tyr Gly Ile Pro Leu
                 85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Gln Leu Gln Gln
            115                 120                 125

Ser Gly Ala Glu Leu Ala Arg Pro Gly Ala Ser Val Lys Leu Ser Cys
            130                 135                 140

Lys Ala Ser Gly Tyr Thr Phe Thr Ser Tyr Trp Met Gln Trp Val Lys
145                 150                 155                 160

Gln Arg Pro Gly Gln Gly Leu Glu Trp Ile Gly Ala Ile Tyr Pro Gly
                165                 170                 175

Asp Gly Asp Thr Arg Tyr Thr Gln Lys Phe Lys Gly Lys Ala Thr Leu
            180                 185                 190

Thr Ala Asp Lys Ser Ser Thr Ala Tyr Met Gln Leu Ser Asn Leu
            195                 200                 205

Thr Ser Glu Asp Ser Ala Val Tyr Tyr Cys Ala Arg Glu Arg Thr Thr
210                 215                 220

Gly Ala Pro Arg Tyr Phe Asp Val Trp Gly Ala Gly Thr Thr Val Thr
225                 230                 235                 240

Val Ser Ser

<210> SEQ ID NO 12
<211> LENGTH: 503
<212> TYPE: PRT
<213> ORGANISM: Artificial
<220> FEATURE:
<223> OTHER INFORMATION: Synthetic Bi38-3 bispecific antibody

<400> SEQUENCE: 12

Asp Ile Gln Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Phe
                 20                  25                  30

Leu Ala Trp Tyr Gln Gln Lys Gln Gly Lys Ser Pro Gln Leu Leu Val
             35                  40                  45

Tyr Asn Thr Lys Thr Leu Thr Glu Gly Val Pro Ser Arg Phe Ser Gly
         50                  55                  60

Ser Gly Ser Gly Thr Gln Phe Ser Leu Lys Ile Asn Asn Leu Gln Pro
 65                  70                  75                  80

Glu Asp Phe Gly Ser Tyr Tyr Cys Gln His His Tyr Gly Ile Pro Leu
                 85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Gln Leu Gln Gln
            115                 120                 125

Ser Gly Ala Glu Leu Ala Arg Pro Gly Ala Ser Val Lys Leu Ser Cys
            130                 135                 140

Lys Ala Ser Gly Tyr Thr Phe Thr Ser Tyr Trp Met Gln Trp Val Lys
145                 150                 155                 160

Gln Arg Pro Gly Gln Gly Leu Glu Trp Ile Gly Ala Ile Tyr Pro Gly
                165                 170                 175
```

```
Asp Gly Asp Thr Arg Tyr Thr Gln Lys Phe Lys Gly Lys Ala Thr Leu
            180                 185                 190

Thr Ala Asp Lys Ser Ser Thr Ala Tyr Met Gln Leu Ser Asn Leu
            195                 200                 205

Thr Ser Glu Asp Ser Ala Val Tyr Tyr Cys Ala Arg Glu Arg Thr Thr
210                 215                 220

Gly Ala Pro Arg Tyr Phe Asp Val Trp Gly Ala Gly Thr Thr Val Thr
225                 230                 235                 240

Val Ser Ser Gly Gly Gly Gly Ser Gly Gly Gly Gly Ser Gly Gly Gly
            245                 250                 255

Gly Ser Asp Ile Lys Leu Gln Gln Ser Gly Ala Glu Leu Ala Arg Pro
            260                 265                 270

Gly Ala Ser Val Lys Met Ser Cys Lys Ala Ser Gly Tyr Thr Phe Thr
            275                 280                 285

Arg Tyr Thr Met His Trp Val Lys Gln Arg Pro Gly Gln Gly Leu Glu
            290                 295                 300

Trp Ile Gly Tyr Ile Asn Pro Ser Arg Gly Tyr Thr Asn Tyr Asn Gln
305                 310                 315                 320

Lys Phe Lys Asp Lys Ala Thr Leu Thr Thr Asp Lys Ser Ser Ser Thr
            325                 330                 335

Ala Tyr Met Gln Leu Ser Ser Leu Thr Ser Glu Asp Ser Ala Val Tyr
            340                 345                 350

Tyr Cys Ala Arg Tyr Tyr Asp Asp His Tyr Cys Leu Asp Tyr Trp Gly
            355                 360                 365

Gln Gly Thr Thr Leu Thr Val Ser Ser Gly Gly Gly Gly Ser Gly Gly
            370                 375                 380

Gly Gly Ser Gly Gly Gly Gly Ser Val Asp Asp Ile Gln Leu Thr Gln
385                 390                 395                 400

Ser Pro Ala Ile Met Ser Ala Ser Pro Gly Glu Lys Val Thr Met Thr
            405                 410                 415

Cys Ser Ala Ser Ser Ser Val Ser Tyr Met Asn Trp Tyr Gln Gln Lys
            420                 425                 430

Ser Gly Thr Ser Pro Lys Arg Trp Ile Tyr Asp Thr Ser Lys Leu Ala
            435                 440                 445

Ser Gly Val Pro Ala His Phe Arg Gly Ser Gly Ser Gly Thr Ser Tyr
            450                 455                 460

Ser Leu Thr Ile Ser Gly Met Glu Ala Glu Asp Ala Ala Thr Tyr Tyr
465                 470                 475                 480

Cys Gln Gln Trp Ser Ser Asn Pro Phe Thr Phe Gly Ser Gly Thr Lys
            485                 490                 495

Leu Glu Leu Lys Ala Ala Ala
            500

<210> SEQ ID NO 13
<211> LENGTH: 442
<212> TYPE: PRT
<213> ORGANISM: Artificial
<220> FEATURE:
<223> OTHER INFORMATION: Synthetic CAR CD38 1G

<400> SEQUENCE: 13

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Phe
            20                  25                  30
```

```
Leu Ala Trp Tyr Gln Gln Lys Gln Gly Lys Ser Pro Gln Leu Leu Val
        35                  40                  45

Tyr Asn Thr Lys Thr Leu Thr Glu Gly Val Pro Ser Arg Phe Ser Gly
    50                  55                  60

Ser Gly Ser Gly Thr Gln Phe Ser Leu Lys Ile Asn Asn Leu Gln Pro
65                  70                  75                  80

Glu Asp Phe Gly Ser Tyr Tyr Cys Gln His His Tyr Gly Ile Pro Leu
                85                  90                  95

Thr Phe Gly Ala Gly Thr Lys Leu Glu Leu Lys Gly Gly Gly Gly Ser
                100                 105                 110

Gly Gly Gly Gly Ser Gly Gly Gly Gly Ser Gln Val Gln Leu Gln Gln
            115                 120                 125

Ser Gly Ala Glu Leu Ala Arg Pro Gly Ala Ser Val Lys Leu Ser Cys
130                 135                 140

Lys Ala Ser Gly Tyr Thr Phe Thr Ser Tyr Trp Met Gln Trp Val Lys
145                 150                 155                 160

Gln Arg Pro Gly Gln Gly Leu Glu Trp Ile Gly Ala Ile Tyr Pro Gly
                165                 170                 175

Asp Gly Asp Thr Arg Tyr Thr Gln Lys Phe Lys Gly Lys Ala Thr Leu
                180                 185                 190

Thr Ala Asp Lys Ser Ser Ser Thr Ala Tyr Met Gln Leu Ser Asn Leu
            195                 200                 205

Thr Ser Glu Asp Ser Ala Val Tyr Tyr Cys Ala Arg Glu Arg Thr Thr
        210                 215                 220

Gly Ala Pro Arg Tyr Phe Asp Val Trp Gly Ala Gly Thr Thr Val Thr
225                 230                 235                 240

Val Ser Ser Leu Glu His Phe Val Pro Val Phe Leu Pro Ala Lys Pro
                245                 250                 255

Thr Thr Thr Pro Ala Pro Arg Pro Pro Thr Pro Ala Pro Thr Ile Ala
                260                 265                 270

Ser Gln Pro Leu Ser Leu Arg Pro Glu Ala Cys Arg Pro Ala Ala Gly
            275                 280                 285

Gly Ala Val His Thr Arg Gly Leu Asp Phe Ala Cys Asp Ile Tyr Ile
290                 295                 300

Trp Ala Pro Leu Ala Gly Thr Cys Gly Val Leu Leu Leu Ser Leu Val
305                 310                 315                 320

Ile Thr Leu Tyr Cys Asn His Arg Asn Arg Val Lys Phe Ser Arg Ser
                325                 330                 335

Ala Asp Ala Pro Ala Tyr Gln Gln Gly Gln Asn Gln Leu Tyr Asn Glu
                340                 345                 350

Leu Asn Leu Gly Arg Arg Glu Glu Tyr Asp Val Leu Asp Lys Arg Arg
            355                 360                 365

Gly Arg Asp Pro Glu Met Gly Gly Lys Pro Gln Arg Arg Lys Asn Pro
370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
                420                 425                 430

Ala Leu His Met Gln Ala Leu Pro Pro Arg
            435                 440
```

```
<210> SEQ ID NO 14
<211> LENGTH: 508
<212> TYPE: PRT
<213> ORGANISM: Artificial
<220> FEATURE:
<223> OTHER INFORMATION: Synthetic CAR CD38 3G

<400> SEQUENCE: 14
```

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Phe
            20                  25                  30

Leu Ala Trp Tyr Gln Gln Lys Gly Lys Ser Pro Gln Leu Leu Val
        35                  40                  45

Tyr Asn Thr Lys Thr Leu Thr Glu Gly Val Pro Ser Arg Phe Ser Gly
    50                  55                  60

Ser Gly Ser Gly Thr Gln Phe Ser Leu Lys Ile Asn Asn Leu Gln Pro
65                  70                  75                  80

Glu Asp Phe Gly Ser Tyr Tyr Cys Gln His Tyr Gly Ile Pro Leu
                85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Gln Leu Gln Gln
        115                 120                 125

Ser Gly Ala Glu Leu Ala Arg Pro Gly Ala Ser Val Lys Leu Ser Cys
130                 135                 140

Lys Ala Ser Gly Tyr Thr Phe Thr Ser Tyr Trp Met Gln Trp Val Lys
145                 150                 155                 160

Gln Arg Pro Gly Gln Gly Leu Glu Trp Ile Gly Ala Ile Tyr Pro Gly
                165                 170                 175

Asp Gly Asp Thr Arg Tyr Thr Gln Lys Phe Lys Gly Lys Ala Thr Leu
            180                 185                 190

Thr Ala Asp Lys Ser Ser Ser Thr Ala Tyr Met Gln Leu Ser Asn Leu
        195                 200                 205

Thr Ser Glu Asp Ser Ala Val Tyr Tyr Cys Ala Arg Glu Arg Thr Thr
    210                 215                 220

Gly Ala Pro Arg Tyr Phe Asp Val Trp Gly Ala Gly Thr Thr Val Thr
225                 230                 235                 240

Val Ser Ser Leu Glu Ile Glu Val Met Tyr Pro Pro Tyr Leu Asp
                245                 250                 255

Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Lys Arg Gly Arg Lys Lys Leu Leu Tyr Ile Phe Lys Gln Pro Phe Met
        355                 360                 365

Arg Pro Val Gln Thr Thr Gln Glu Glu Asp Gly Cys Ser Cys Arg Phe
370                 375                 380

Pro Glu Glu Glu Gly Gly Cys Glu Leu Gly Ser Arg Val Lys Phe
385                 390                 395                 400

Ser Arg Ser Ala Asp Ala Pro Ala Tyr Gln Gln Gly Gln Asn Gln Leu
            405                 410                 415

Tyr Asn Glu Leu Asn Leu Gly Arg Arg Glu Glu Tyr Asp Val Leu Asp
        420                 425                 430

Lys Arg Gly Arg Asp Pro Glu Met Gly Gly Lys Pro Arg Arg Lys
    435                 440                 445

Asn Pro Gln Glu Gly Leu Tyr Asn Glu Leu Gln Lys Asp Lys Met Ala
450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 15
<211> LENGTH: 545
<212> TYPE: PRT
<213> ORGANISM: Artificial
<220> FEATURE:
<223> OTHER INFORMATION: Synthetic Bi38-3 + leader sequence

<400> SEQUENCE: 15

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ala Ser Leu
            20                  25                  30

Ser Ala Ser Val Gly Glu Thr Val Thr Ile Thr Cys Arg Ala Ser Glu
        35                  40                  45

Asn Ile Tyr Ser Phe Leu Ala Trp Tyr Gln Gln Lys Gln Gly Lys Ser
50                  55                  60

Pro Gln Leu Leu Val Tyr Asn Thr Lys Thr Leu Thr Glu Gly Val Pro
65                  70                  75                  80

Ser Arg Phe Ser Gly Ser Gly Ser Gly Thr Gln Phe Ser Leu Lys Ile
                85                  90                  95

Asn Asn Leu Gln Pro Glu Asp Phe Gly Ser Tyr Tyr Cys Gln His His
            100                 105                 110

Tyr Gly Ile Pro Leu Thr Phe Gly Ala Gly Thr Lys Leu Glu Leu Lys
        115                 120                 125

Gly Gly Gly Gly Ser Gly Gly Gly Ser Gly Gly Gly Gly Ser Gln
130                 135                 140

Val Gln Leu Gln Gln Ser Gly Ala Glu Leu Ala Arg Pro Gly Ala Ser
145                 150                 155                 160

Val Lys Leu Ser Cys Lys Ala Ser Gly Tyr Thr Phe Thr Ser Tyr Trp
                165                 170                 175

Met Gln Trp Val Lys Gln Arg Pro Gly Gln Gly Leu Glu Trp Ile Gly
            180                 185                 190

Ala Ile Tyr Pro Gly Asp Gly Asp Thr Arg Tyr Thr Gln Lys Phe Lys
        195                 200                 205

Gly Lys Ala Thr Leu Thr Ala Asp Lys Ser Ser Ser Thr Ala Tyr Met
    210                 215                 220

```
Gln Leu Ser Asn Leu Thr Ser Glu Asp Ser Ala Val Tyr Tyr Cys Ala
225                 230                 235                 240

Arg Glu Arg Thr Thr Gly Ala Pro Arg Tyr Phe Asp Val Trp Gly Ala
            245                 250                 255

Gly Thr Thr Val Thr Val Ser Ser Gly Gly Gly Gly Ser Gly Gly Gly
            260                 265                 270

Gly Ser Gly Gly Gly Gly Ser Asp Ile Lys Leu Gln Gln Ser Gly Ala
        275                 280                 285

Glu Leu Ala Arg Pro Gly Ala Ser Val Lys Met Ser Cys Lys Ala Ser
    290                 295                 300

Gly Tyr Thr Phe Thr Arg Tyr Thr Met His Trp Val Lys Gln Arg Pro
305                 310                 315                 320

Gly Gln Gly Leu Glu Trp Ile Gly Tyr Ile Asn Pro Ser Arg Gly Tyr
            325                 330                 335

Thr Asn Tyr Asn Gln Lys Phe Lys Asp Lys Ala Thr Leu Thr Thr Asp
        340                 345                 350

Lys Ser Ser Ser Thr Ala Tyr Met Gln Leu Ser Ser Leu Thr Ser Glu
    355                 360                 365

Asp Ser Ala Val Tyr Tyr Cys Ala Arg Tyr Tyr Asp Asp His Tyr Cys
370                 375                 380

Leu Asp Tyr Trp Gly Gln Gly Thr Thr Leu Thr Val Ser Ser Gly Gly
385                 390                 395                 400

Gly Gly Ser Gly Gly Gly Gly Ser Gly Gly Gly Gly Ser Val Asp Asp
            405                 410                 415

Ile Gln Leu Thr Gln Ser Pro Ala Ile Met Ser Ala Ser Pro Gly Glu
        420                 425                 430

Lys Val Thr Met Thr Cys Ser Ala Ser Ser Ser Val Ser Tyr Met Asn
    435                 440                 445

Trp Tyr Gln Gln Lys Ser Gly Thr Ser Pro Lys Arg Trp Ile Tyr Asp
    450                 455                 460

Thr Ser Lys Leu Ala Ser Gly Val Pro Ala His Phe Arg Gly Ser Gly
465                 470                 475                 480

Ser Gly Thr Ser Tyr Ser Leu Thr Ile Ser Gly Met Glu Ala Glu Asp
            485                 490                 495

Ala Ala Thr Tyr Tyr Cys Gln Gln Trp Ser Ser Asn Pro Phe Thr Phe
        500                 505                 510

Gly Ser Gly Thr Lys Leu Glu Leu Lys Ala Ala Ala Glu Gln Lys Leu
    515                 520                 525

Ile Ser Glu Glu Asp Leu Asn Gly Ala Val Glu His His His His
    530                 535                 540

His
545

<210> SEQ ID NO 16
<211> LENGTH: 463
<212> TYPE: PRT
<213> ORGANISM: Artificial
<220> FEATURE:
<223> OTHER INFORMATION: Synthetic CAR CD38 1G + leader sequence

<400> SEQUENCE: 16

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ala Ser Leu
            20                  25                  30
```

-continued

Ser Ala Ser Val Gly Glu Thr Val Thr Ile Thr Cys Arg Ala Ser Glu
         35                  40                  45

Asn Ile Tyr Ser Phe Leu Ala Trp Tyr Gln Gln Lys Gln Gly Lys Ser
         50                  55                  60

Pro Gln Leu Leu Val Tyr Asn Thr Lys Thr Leu Thr Glu Gly Val Pro
65                   70                  75                  80

Ser Arg Phe Ser Gly Ser Gly Ser Gly Thr Gln Phe Ser Leu Lys Ile
                 85                  90                  95

Asn Asn Leu Gln Pro Glu Asp Phe Gly Ser Tyr Tyr Cys Gln His His
            100                 105                 110

Tyr Gly Ile Pro Leu Thr Phe Gly Ala Gly Thr Lys Leu Glu Leu Lys
        115                 120                 125

Gly Gly Gly Gly Ser Gly Gly Gly Ser Gly Gly Gly Ser Gln
    130                 135                 140

Val Gln Leu Gln Gln Ser Gly Ala Glu Leu Ala Arg Pro Gly Ala Ser
145                 150                 155                 160

Val Lys Leu Ser Cys Lys Ala Ser Gly Tyr Thr Phe Thr Ser Tyr Trp
                165                 170                 175

Met Gln Trp Val Lys Gln Arg Pro Gly Gln Gly Leu Glu Trp Ile Gly
            180                 185                 190

Ala Ile Tyr Pro Gly Asp Gly Asp Thr Arg Tyr Thr Gln Lys Phe Lys
        195                 200                 205

Gly Lys Ala Thr Leu Thr Ala Asp Lys Ser Ser Thr Ala Tyr Met
    210                 215                 220

Gln Leu Ser Asn Leu Thr Ser Glu Asp Ser Ala Val Tyr Tyr Cys Ala
225                 230                 235                 240

Arg Glu Arg Thr Thr Gly Ala Pro Arg Tyr Phe Asp Val Trp Gly Ala
                245                 250                 255

Gly Thr Thr Val Thr Val Ser Ser Leu Glu His Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
        290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
        370                 375                 380

Leu Asp Lys Arg Arg Gly Arg Asp Pro Glu Met Gly Gly Lys Pro Gln
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg

<210> SEQ ID NO 17
<211> LENGTH: 529
<212> TYPE: PRT
<213> ORGANISM: Artificial
<220> FEATURE:
<223> OTHER INFORMATION: Synthetic CAR CD38 3G + leader sequence

<400> SEQUENCE: 17

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ala Ser Leu
            20                  25                  30

Ser Ala Ser Val Gly Glu Thr Val Thr Ile Thr Cys Arg Ala Ser Glu
        35                  40                  45

Asn Ile Tyr Ser Phe Leu Ala Trp Tyr Gln Gln Lys Gln Gly Lys Ser
    50                  55                  60

Pro Gln Leu Leu Val Tyr Asn Thr Lys Thr Leu Thr Glu Gly Val Pro
65                  70                  75                  80

Ser Arg Phe Ser Gly Ser Gly Ser Gly Thr Gln Phe Ser Leu Lys Ile
                85                  90                  95

Asn Asn Leu Gln Pro Glu Asp Phe Gly Ser Tyr Tyr Cys Gln His His
            100                 105                 110

Tyr Gly Ile Pro Leu Thr Phe Gly Ala Gly Thr Lys Leu Glu Leu Lys
        115                 120                 125

Gly Gly Gly Gly Ser Gly Gly Gly Ser Gly Gly Gly Gly Ser Gln
    130                 135                 140

Val Gln Leu Gln Gln Ser Gly Ala Glu Leu Ala Arg Pro Gly Ala Ser
145                 150                 155                 160

Val Lys Leu Ser Cys Lys Ala Ser Gly Tyr Thr Phe Thr Ser Tyr Trp
                165                 170                 175

Met Gln Trp Val Lys Gln Arg Pro Gly Gln Gly Leu Glu Trp Ile Gly
            180                 185                 190

Ala Ile Tyr Pro Gly Asp Gly Asp Thr Arg Tyr Thr Gln Lys Phe Lys
        195                 200                 205

Gly Lys Ala Thr Leu Thr Ala Asp Lys Ser Ser Thr Ala Tyr Met
    210                 215                 220

Gln Leu Ser Asn Leu Thr Ser Glu Asp Ser Ala Val Tyr Tyr Cys Ala
225                 230                 235                 240

Arg Glu Arg Thr Thr Gly Ala Pro Arg Tyr Phe Asp Val Trp Gly Ala
                245                 250                 255

Gly Thr Thr Val Thr Val Ser Ser Leu Glu Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
    290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe

-continued

```
                355                 360                 365
Ala Ala Tyr Arg Ser Lys Arg Gly Arg Lys Lys Leu Leu Tyr Ile Phe
    370                 375                 380
Lys Gln Pro Phe Met Arg Pro Val Gln Thr Thr Gln Glu Glu Asp Gly
385                 390                 395                 400
Cys Ser Cys Arg Phe Pro Glu Glu Glu Glu Gly Gly Cys Glu Leu Gly
                405                 410                 415
Ser Arg Val Lys Phe Ser Arg Ser Ala Asp Ala Pro Ala Tyr Gln Gln
            420                 425                 430
Gly Gln Asn Gln Leu Tyr Asn Glu Leu Asn Leu Gly Arg Arg Glu Glu
        435                 440                 445
Tyr Asp Val Leu Asp Lys Arg Gly Arg Asp Pro Glu Met Gly Gly
    450                 455                 460
Lys Pro Arg Arg Lys Asn Pro Gln Glu Gly Leu Tyr Asn Glu Leu Gln
465                 470                 475                 480
Lys Asp Lys Met Ala Glu Ala Tyr Ser Glu Ile Gly Met Lys Gly Glu
                485                 490                 495
Arg Arg Arg Gly Lys Gly His Asp Gly Leu Tyr Gln Gly Leu Ser Thr
            500                 505                 510
Ala Thr Lys Asp Thr Tyr Asp Ala Leu His Met Gln Ala Leu Pro Pro
        515                 520                 525
Arg
```

<210> SEQ ID NO 18
<211> LENGTH: 415
<212> TYPE: PRT
<213> ORGANISM: Artificial
<220> FEATURE:
<223> OTHER INFORMATION: Synthetic CCR - CD38

<400> SEQUENCE: 18

```
Met Ala Leu Pro Val Thr Ala Leu Leu Leu Pro Leu Ala Leu Leu Leu
1               5                   10                  15
His Ala Ala Arg Pro Asp Ile Gln Met Thr Gln Ser Pro Ala Ser Leu
            20                  25                  30
Ser Ala Ser Val Gly Glu Thr Val Thr Ile Thr Cys Arg Ala Ser Glu
        35                  40                  45
Asn Ile Tyr Ser Phe Leu Ala Trp Tyr Gln Gln Lys Gln Gly Lys Ser
    50                  55                  60
Pro Gln Leu Leu Val Tyr Asn Thr Lys Thr Leu Thr Glu Gly Val Pro
65                  70                  75                  80
Ser Arg Phe Ser Gly Ser Gly Ser Gly Thr Gln Phe Ser Leu Lys Ile
                85                  90                  95
Asn Asn Leu Gln Pro Glu Asp Phe Gly Ser Tyr Tyr Cys Gln His His
            100                 105                 110
Tyr Gly Ile Pro Leu Thr Phe Gly Ala Gly Thr Lys Leu Glu Leu Lys
        115                 120                 125
Gly Gly Gly Gly Ser Gly Gly Gly Gly Ser Gly Gly Gly Gly Ser Gln
    130                 135                 140
Val Gln Leu Gln Gln Ser Gly Ala Glu Leu Ala Arg Pro Gly Ala Ser
145                 150                 155                 160
Val Lys Leu Ser Cys Lys Ala Ser Gly Tyr Thr Phe Thr Ser Tyr Trp
                165                 170                 175
Met Gln Trp Val Lys Gln Arg Pro Gly Gln Gly Leu Glu Trp Ile Gly
            180                 185                 190
```

Ala Ile Tyr Pro Gly Asp Gly Asp Thr Arg Tyr Thr Gln Lys Phe Lys
         195                 200                 205

Gly Lys Ala Thr Leu Thr Ala Asp Lys Ser Ser Thr Ala Tyr Met
    210                 215                 220

Gln Leu Ser Asn Leu Thr Ser Glu Asp Ser Ala Val Tyr Tyr Cys Ala
225                 230                 235                 240

Arg Glu Arg Thr Thr Gly Ala Pro Arg Tyr Phe Asp Val Trp Gly Ala
                245                 250                 255

Gly Thr Thr Val Thr Val Ser Ser Leu Glu Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
    290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Lys Arg Gly Arg Lys Lys Leu Leu Tyr Ile Phe
    370                 375                 380

Lys Gln Pro Phe Met Arg Pro Val Gln Thr Thr Gln Glu Glu Asp Gly
385                 390                 395                 400

Cys Ser Cys Arg Phe Pro Glu Glu Glu Glu Gly Gly Cys Glu Leu
                405                 410                 415

<210> SEQ ID NO 19
<211> LENGTH: 21
<212> TYPE: PRT
<213> ORGANISM: Artificial
<220> FEATURE:
<223> OTHER INFORMATION: Synthetic Leader CD8a

<400> SEQUENCE: 19

Met Ala Leu Pro Val Thr Ala Leu Leu Leu Pro Leu Ala Leu Leu Leu
1               5                   10                  15

His Ala Ala Arg Pro
            20

<210> SEQ ID NO 20
<211> LENGTH: 264
<212> TYPE: PRT
<213> ORGANISM: Artificial
<220> FEATURE:
<223> OTHER INFORMATION: Synthetic Anti-CD38 scFv (Table 1)

<400> SEQUENCE: 20

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ala Ser Leu
            20                  25                  30

Ser Ala Ser Val Gly Glu Thr Val Thr Ile Thr Cys Arg Ala Ser Glu
        35                  40                  45

Asn Ile Tyr Ser Phe Leu Ala Trp Tyr Gln Gln Lys Gln Gly Lys Ser

-continued

```
                50                  55                  60
Pro Gln Leu Leu Val Tyr Asn Thr Lys Thr Leu Thr Glu Gly Val Pro
65                      70                  75                  80

Ser Arg Phe Ser Gly Ser Gly Ser Gly Thr Gln Phe Ser Leu Lys Ile
                    85                  90                  95

Asn Asn Leu Gln Pro Glu Asp Phe Gly Ser Tyr Tyr Cys Gln His His
                100                 105                 110

Tyr Gly Ile Pro Leu Thr Phe Gly Ala Gly Thr Lys Leu Glu Leu Lys
            115                 120                 125

Gly Gly Gly Gly Ser Gly Gly Gly Ser Gly Gly Gly Gly Ser Gln
        130                 135                 140

Val Gln Leu Gln Gln Ser Gly Ala Glu Leu Ala Arg Pro Gly Ala Ser
145                 150                 155                 160

Val Lys Leu Ser Cys Lys Ala Ser Gly Tyr Thr Phe Thr Ser Tyr Trp
                165                 170                 175

Met Gln Trp Val Lys Gln Arg Pro Gly Gln Gly Leu Glu Trp Ile Gly
                180                 185                 190

Ala Ile Tyr Pro Gly Asp Gly Asp Thr Arg Tyr Thr Gln Lys Phe Lys
            195                 200                 205

Gly Lys Ala Thr Leu Thr Ala Asp Lys Ser Ser Ser Thr Ala Tyr Met
        210                 215                 220

Gln Leu Ser Asn Leu Thr Ser Glu Asp Ser Ala Val Tyr Tyr Cys Ala
225                 230                 235                 240

Arg Glu Arg Thr Thr Gly Ala Pro Arg Tyr Phe Asp Val Trp Gly Ala
                245                 250                 255

Gly Thr Thr Val Thr Val Ser Ser
                260
```

ANTIBODIES HAVING SPECIFICITY FOR CD38 AND USES THEREOF

FIELD OF THE INVENTION

The present invention is in the field of medicine, and in particular in the field of oncology.

BACKGROUND OF THE INVENTION

CD38 is a type II transmembrane glycoprotein. The functions of CD38 include both receptor mediation in adhesion and signaling events as well as enzymatic activity. CD38 is normally found on hemopoietic cells and in solid tissues. With regard to hemopoietic cells, the majority of medullary thymocytes are CD38$^+$, resting and circulating T- and B-cells are CD38$^-$ and activated cells are CD38$^+$. CD38 is also expressed on approximately 80% of resting NK cells and monocytes and on lymph node germinal center lymphoblasts, plasma B cells and some intrafollicular cells. CD38 can also be expressed by dendritic cells. A significant proportion of normal bone marrow cells, particular precursor cells, express CD38. In addition, 50-80% of umbilical cord blood cells is CD38$^+$ and remains so in human blood for the first two to three years of life. In addition to lymphoid precursor cells, CD38 is also expressed on erythrocytes and on platelets. With regard to solid tissues, CD38 is expressed in the gut by intra-epithelial cells and lamina propria lymphocytes, by Purkinje cells and neurofibrillary tangles in the brain, by epithelial cells in the prostate, β-cells in the pancreas, osteoclasts in the bone, retinal cells in the eye, and sarcolemma of smooth and striated muscle.

CD38 is also expressed in a variety of malignant hematological diseases, including multiple myeloma, B-cell chronic lymphocytic leukemia, B-cell acute lymphocytic leukemia, Waldenström macroglobulinemia, primary systemic amyloidosis, mantle-cell lymphoma, pro-lymphocytic/myelocytic leukemia, acute myeloid leukemia, chronic myeloid leukemia, follicular lymphoma, NK-cell leukemia and plasma-cell leukemia. For instance, multiple Myeloma (MM) is a heterogeneous hematologic malignancy characterized by the accumulation in the bone marrow of patients of tumor plasma cells secreting a monoclonal immunoglobulin, as well as osteolytic lesions[1]. Current treatments have raised the median overall survival to around 6 years, and the recent development of monoclonal antibodies (mAb), such as elotuzumab (anti-SLAMF7) and daratumumab (anti-CD38) has further improved outcomes[2-4]. However, the overall survival of patients with relapsed disease after proteasome inhibitors (PIs), Immunomodulators (IMIDs) and mAb treatments is still extremely poor and MM remains an incurable disease. Thus, novel therapeutic strategies are needed to improve patient care and, eventually, to develop curative treatments.

Several anti-CD38 antibodies are described in the literature, for instance in Lande R, et al., Cell Immunol. 220 (1), 30-8 (2002), Ausiello C M, et al., Tissue Antigens. 56 (6), 539-47 (2000), and Cotner T, et al., Int J Immunopharmacol. 3 (3), 255-68 (1981). For instance WO2006099875 describes several human anti-CD38 antibodies.

SUMMARY OF THE INVENTION

As defined by the claims, the present invention relates to antibodies having specificity for CD38 and uses thereof.

DETAILED DESCRIPTION OF THE INVENTION

The inventors have developed a new anti-CD38/CD3 Bispecific T cell-engager antibody, which triggers specific T-cell mediated lysis of CD38-positive MM cells in vitro, ex vivo and in vivo. This new anti-CD38/CD3 Bispecific T cell-engager antibody, Bi 38-3, mediated T cell killing of MM cells will not be affected by the mechanisms of resistance to anti-CD38 mAbs (such as Daratumumab, an anti CD-38 mab approved for the treatment of MM) which are associated with binding of the therapeutic antibody to FcγR. The inventors demonstrated that Bi38-3 mediates autologous T cell mediated killing of tumor plasma cell from patients at diagnosis and at relapse with similar efficiencies. Moreover, they demonstrated that Bi38-3 has no significant effect on T, B and NK cells in vitro, it readily induced T cell mediated killing of MM cells, while preserving B cells from T cell cytotoxic activity. They showed that Bi38-3 was able to trigger a six-fold reduction in tumor burden in only 3 days in vivo. Thus, the inventors demonstrated that Bi 38-3 is a selective and efficient compound in the treatment of MM, that could be used both front line or at relapse, and support further evaluation in MM patients.

Main Definitions

As used herein, the term "CD38" has its general meaning in the art and refers to the ADP-ribosyl cyclase/cyclic ADP-ribose hydrolase 1. An exemplary amino acid sequence for CD38 is represented by SEQ ID NO:1. The extracellular domain of CD38 ranges from the amino acid residue at position 43 to the amino acid residue at position 300 in SEQ ID NO:1.

```
>sp|P28907|CD38_HUMAN ADP-ribosyl cyclase/cyclic ADP-ribose
hydrolase 1 OS = Homo sapiens OX = 9606 GN = CD38 PE = 1 SV = 2
                                                          SEQ ID NO: 1
MANCEFSPVSGDKPCCRLSRRAQLCLGVSILVLILVVVLAVVVPRWRQQWSGPGTTKRFP

ETVLARCVKYTEIHPEMRHVDCQSVWDAFKGAFISKHPCNITEEDYQPLMKLGTQTVPCN

KILLWSRIKDLAHQFTQVQRDMFTLEDILLGYLADDLTWCGEFNTSKINYQSCPDWRKDC

SNNPVSVFWKTVSRRFAEAACDVVHVMLNGSRSKIFDKNSTFGSVEVHNLQPEKVQTLEA

WVIHGGREDSRDLCQDPTIKELESIISKRNIQFSCKNIYRPDKFLQCVKNPEDSSCTSEI
```

As used herein, the term "CD3" has its general meaning in the art and refers to the CD3 (cluster of differentiation 3) T cell co-receptor that helps to activate both the cytotoxic T cell (CD8+ naive T cells) and also T helper cells (CD4+ naive T cells). It consists of a protein complex and is composed of four distinct chains. In mammals, the complex contains a CD3γ chain, a CD3δ chain, and two CD3ε chains.

These chains associate with the T-cell receptor (TCR) and the ζ-chain (zeta-chain) to generate an activation signal in T lymphocytes. The TCR, ζ-chain, and CD3 molecules together constitute the TCR complex. An exemplary amino acid sequence for CD3ε is represented by SEQ ID NO:2. The extracellular domain of CD3ε ranges from the amino acid residue at position 23 to the amino acid residue at position 207 in SEQ ID NO:2.

three to four constant domains (CH1, CH2, CH3 and CH4 collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment

```
>sp|P07766|CD3E_HUMAN T-cell surface glycoprotein CD3 epsilon
chain OS = Homo sapiens OX = 9606 GN = CD3E PE = 1 SV = 2
                                                           SEQ ID NO: 2
MQSGTHWRVLGLCLLSVGVWGQDGNEEMGGITQTPYKVSISGTTVILTCPQYPGSEILWQ

HNDKNIGGDEDDKNIGSDEDHLSLKEFSELEQSGYYVCYPRGSKPEDANFYLYLRARVCE

NCMEMDVMSVATIVIVDICITGGLLLLVYYWSKNRKAKAKPVTRGAGAGGRQRGQNKERP

PPVPNPDYEPIRKGQRDLYSGLNQRRI
```

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four (α, δ, γ) to five (μ, ε) domains, a variable domain (VH) and is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) can participate to the antibody binding site or influence the overall domain structure and hence the combining site. CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (VH-CDR1), residues 50-65 (VH-CDR2) and residues 95-102 (VH-CDR3) according to the Kabat numbering system. The CDRs of the light chain variable domain are located at residues 24-34 (VL-CDR1), residues 50-56 (VL-CDR2) and residues 89-97 (VL-CDR3) according to the Kabat numbering system.

As used herein, the term "BB51 antibody" refers to the murine antibody characterized by the variable domain of the heavy chain as set forth in SEQ ID NO:3 and the variable domain of the light chain as set forth in SEQ ID NO:4.

>IgH VH1.87-D1.1-J1:
SEQ ID NO: 3
QVQLQQSGAELARPGASVKLSCKASGYTFTSYWMQWVKQRPGQGLEWIGA

IYPGDGDTRYTQKFKGKATLTADKSSSTAYMQLSNLTSEDSAVYYCARER

TTGAPRYFDVWGAGTTVTVSS

>Igk Vk12.44-Jk5:
SEQ ID NO: 4
DIQMTQSPASLSASVGETVTITCRASENTYSFLAWYQQKQGKSPQLLVYN

TKTLTEGVPSRFSGSGSGTQFSLKINNLQPEDFGSYYCQHHYGIPLTFGA

GTKLELK

As used herein, the term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL. As used herein, the terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

As used herein, the term "chimeric antibody" refers to an antibody which comprises a VH domain and a VL domain of a non-human antibody, and a CH domain and a CL domain of a human antibody. In some embodiments, a "chimeric antibody" is an antibody molecule in which (a) the constant region (i.e., the heavy and/or light chain), or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Chimeric antibodies also include primatized and in particular humanized antibodies. Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992). (see U.S. Pat. No. 4,816,567; and Morrison et al., Proc. Natl. Acad. Sci. USA, 81:6851-6855 (1984)).

As used herein, the term "humanized antibody" refers to an antibody having variable region framework and constant regions from a human antibody but retains the CDRs of a previous non-human antibody. In some embodiments, a humanized antibody contains minimal sequence derived from non-human immunoglobulin. For the most part, humanized antibodies and antibody fragments thereof may be human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. Such antibodies are designed to maintain the binding specificity of the non-human antibody from which the binding regions are derived, but to avoid an immune reaction against the non-human antibody. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

As used herein, the term "binding" in the context of the binding of an antibody to a predetermined antigen or epitope typically is a binding with a low affinity corresponding to a $K_D$ of about $10^{-6}$ M when determined by for instance surface plasmon resonance (SPR) technology in a BIAcore 3000 instrument using a soluble form of the antigen as the ligand and the antibody as the analyte. BIACORE® (GE Healthcare, Piscaataway, NJ) is one of a variety of surface plasmon resonance assay formats that are routinely used to epitope bin panels of monoclonal antibodies. Typically, an antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein), which is not identical or closely related to the predetermined antigen. When the $K_D$ of the antibody is very low (that is, the antibody has a high affinity), then the $K_D$ with which it binds the antigen is typically at least 10,000-fold lower than its $K_D$ for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

As used herein, the term "bispecific antibody" has its general meaning in the art and refers to an artificial, hybrid antibody having two different pairs of heavy and light chain and also two different antigen-binding sites.

As used herein, the term "Bispecific T-cell engager" or "BiTE" refers to a bispecific antibody that is a recombinant protein construct composed of two flexibly connected single-chain antibodies (scFv). One of said scFv antibodies binds specifically to a selected, target cell-expressed tumour antigen, the second binds specifically to another molecule such as CD3, a subunit of the T-cell receptor complex on T cells. In some embodiments, the BiTE antibodies are capable of binding T cells transiently to target cells and, at the same time, activating the cytolytic activity of the T cells. The BiTE-mediated activation of the T cells requires neither specific T-cell receptors on the T cells, nor MHC I molecules, peptide antigens or co-stimulatory molecules on the target cell.

As used herein the term "CAR-T cell" refers to a T lymphocyte that has been genetically engineered to express a CAR. The definition of CAR T-cells encompasses all classes and subclasses of T-lymphocytes including CD4+, CD8+ T cells, gamma delta T cells as well as effector T cells, memory T cells, regulatory T cells, and the like. The T lymphocytes that are genetically modified may be "derived" or "obtained" from the subject who will receive the treatment using the genetically modified T cells or they may "derived" or "obtained" from a different subject.

As used herein, the term "Chimeric Antigen Receptor" or "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In some embodiments, the stimulatory molecule is the zeta chain associated with the T cell receptor complex. In some embodiments, the cytoplasmic signaling domain further comprises one or more functional signaling domains derived from at least one costimulatory molecule as defined below. In some embodiments, the costimulatory molecule is chosen from the costimulatory molecules described herein, e.g., 4-1BB (i.e., CD137), CD27 and/or CD28. In some embodiments, the CAR comprises a chimeric fusion protein comprising an extracellular antigen binding domain, a transmembrane domain and an intracellular signaling domain comprising a functional signaling domain derived from a stimulatory molecule. In some embodiments, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In some embodiments, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In some embodiments, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In some embodiments, the CAR comprises an optional leader sequence at the amino-terminus (N-ter) of the CAR fusion protein. In some embodiments, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane. In particular aspects, CARs comprise fusions of single-chain variable fragments (scFv) derived from monoclonal antibodies, fused to CD3-zeta a transmembrane domain and endodomain. In some embodiments, CARs comprise domains for additional co-stimulatory signaling, such as CD3-zeta, FcR, CD27, CD28, CD137, DAP10, and/or OX40. In some embodiments, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

As used herein, the term "T cells" has its general meaning in the art and represent an important component of the immune system that plays a central role in cell-mediated immunity. T cells are known as conventional lymphocytes as they recognize the antigen with their TCR (T cell receptor for the antigen) with presentation or restriction by molecules of the complex major histocompatibility. There are several subsets of T cells each having a distinct function such as CD8+ T cells, CD4+ T cells, and gamma delta T cells.

As used herein, the term "CD8+ T cell" has its general meaning in the art and refers to a subset of T cells which express CD8 on their surface. They are MHC class I-restricted, and function as cytotoxic T cells. "CD8+ T cells" are also called cytotoxic T lymphocytes (CTL), T-killer cells, cytolytic T cells, or killer T cells. CD8 antigens are members of the immunoglobulin supergene family and are associative recognition elements in major histocompatibility complex class I-restricted interactions. As used herein, the term "tumor infiltrating CD8+ T cell" refers to the pool of CD8+ T cells of the patient that have left the blood stream and have migrated into a tumor.

As used herein, the term "CD4+ T cells" (also called T helper cells or TH cells) refers to T cells which express the CD4 glycoprotein on their surfaces and which assist other white blood cells in immunologic processes, including maturation of B cells into plasma cells and memory B cells, and activation of cytotoxic T cells and macrophages. CD4+ T cells become activated when they are presented with peptide antigens by MHC class II molecules, which are expressed on the surface of antigen-presenting cells (APCs). Once activated, they divide rapidly and secrete cytokines that regulate or assist in the active immune response. These cells can differentiate into one of several subtypes, including TH1, TH2, TH3, TH17, TH9, TFH or Treg, which secrete different cytokines to facilitate different types of immune responses. Signaling from the APC directs T cells into particular subtypes. In addition to CD4, the TH cell surface biomarkers known in the art include CXCR3 (Th1), CCR4, Crth2 (Th2), CCR6 (Th17), CXCR5 (Tfh) and as well as subtype-specific expression of cytokines and transcription factors including T-bet, GATA3, EOMES, RORγT, BCL6 and FoxP3.

As used herein, the term "gamma delta T cell" has its general meaning in the art. Gamma delta T cells normally account for 1 to 5% of peripheral blood lymphocytes in a healthy individual (human, monkey). They are involved in mounting a protective immune response, and it has been shown that they recognize their antigenic ligands by a direct interaction with antigen, without any presentation by WIC molecules of antigen-presenting cells. Gamma 9 delta 2 T cells (sometimes also called gamma 2 delta 2 T cells) are gamma delta T cells bearing TCR receptors with the variable domains Vγ9 and Vδ2. They form the majority of gamma delta T cells in human blood. When activated, gamma delta T cells exert potent, non-MHC restricted cytotoxic activity, especially efficient at killing various types of cells, particularly pathogenic cells. These may be cells infected by a virus (Poccia et al., J. Leukocyte Biology, 1997, 62: 1-5) or by other intracellular parasites, such as mycobacteria (Constant et al., Infection and Immunity, December 1995, vol. 63, no. 12: 4628-4633) or protozoa (Behr et al., Infection and Immunity, 1996, vol. 64, no. 8: 2892-2896). They may also be cancer cells (Poccia et al., J. Immunol., 159: 6009-6015; Fournie and Bonneville, Res. Immunol., 66th Forum in Immunology, 147: 338-347). The possibility of modulating the activity of said cells in vitro, ex vivo or in vivo would therefore provide novel, effective therapeutic approaches in the treatment of various pathologies such as infectious diseases (particularly viral or parasitic), cancers, allergies, and even autoimmune and/or inflammatory disorders.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein, the term "cancer" has its general meaning in the art and refers to an abnormal cell having the capacity for autonomous growth, i.e., an abnormal state or condition characterized by rapidly proliferating cell growth with the potential to invade or spread to other parts of the body. The term is meant to include all types of cancerous growths or oncogenic processes, metastatic tissues or malignantly transformed cells, tissues, or organs, irrespective of histopathologic type or stage of invasiveness. The terms "cancer" include, but is not limited to, malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, glioblastoma non-small cell carcinoma of the lung, cancer of the small intestine and cancer of the esophagus. The term "cancer" includes also, but is not limited to, solid tumors and blood-borne tumors.

The term "solid cancer" has its general meaning in the art and refers to solid cancer selected from the group consisting of, but not limited to, head and neck squamous cell carcinoma (HNSCC), adrenal cortical cancer, anal cancer, bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), cervical cancer, colorectal cancer, endometrial cancer (e.g. endometrial adenocarcinoma, adenocanthoma, papillary serous adnocarcinoma, clear cell), esophagus cancer, gallbladder cancer (mucinous adenocarcinoma, small cell carcinoma), gastrointestinal carcinoid tumors (e.g. choriocarcinoma, chorioadenoma destruens), Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma), vaginal cancer, vulvar cancer, and uterine cancer (e.g. uterine leiomyosarcoma).

The term "blood-borne cancer", or leukemias, has its general meaning in the art and refers cancers of the blood cells. They start in the bone marrow, the soft tissue in the center of bones where blood cells are made. With leukemia, the bone marrow begins to make abnormal cells that crowd out the normal blood cells.

In some embodiment, the cancer is CD38-positive hematological malignancy.

As uses herein, the term "CD38-positive hematological malignancy" refers to a hematological malignancy characterized by the presence of tumor cells expressing CD38 including leukemias, lymphomas and myeloma. Examples of such CD38-positive hematological malignancies include precursor B-cell lymphoblastic leukemia/lymphoma and B-cell non-Hodgkin's lymphoma; acute promyelocytic leukemia, acute lymphoblastic leukemia and mature B-cell neoplasms, such as B-cell chronic lymphocytic leukemia (CLL)/small lymphocytic lymphoma (SLL), B-cell acute lymphocytic leukemia, B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, multiple myeloma, plasma cell leukemia, post-transplant lymphoproliferative disorder, Waldenstrom's macroglobulinemia, plasma cell leukemias and anaplastic large-cell lymphoma (ALCL).

In some embodiment, the CD38-positive hematological malignancy is multiple myeloma.

As used herein, the term "therapeutically effective amount" refers to an amount effective, at dosages and for periods of time necessary, to achieve a desired therapeutic result. A therapeutically effective amount of the active agent may vary according to factors such as the disease state, age, sex, and weight of the individual, and the ability of the active agent to elicit a desired response in the individual. A therapeutically effective amount is also one in which any toxic or detrimental effects of the antibody or antibody portion are outweighed by the therapeutically beneficial effects. The efficient dosages and dosage regimens for the active agent depend on the disease or condition to be treated and may be determined by the persons skilled in the art. A physician having ordinary skill in the art may readily determine and prescribe the effective amount of the pharmaceutical composition required. For example, the physician could start doses of active agent employed in the pharmaceutical composition at levels lower than that required achieving the desired therapeutic effect and gradually increasing the dosage until the desired effect is achieved. In general, a suitable dose of a composition of the present invention will be that amount of the compound, which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. Typically, the ability of a compound to inhibit cancer may, for example, be evaluated in an animal model system predictive of efficacy in human tumors. A therapeutically effective amount of a therapeutic compound may decrease tumor size, or otherwise ameliorate symptoms in a patient. One of ordinary skill in the art would be able to determine such amounts based on such factors as the patient's size, the severity of the patient's symptoms, and the particular composition or route of administration selected. An exemplary, non-limiting range for a therapeutically effective amount of a inhibitor of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of a inhibitor of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. In some embodiments, the efficacy may be monitored by visualization of the disease area, or by other diagnostic methods described further herein, e.g. by performing one or more PET-CT scans, for example using a labeled inhibitor of the present invention, fragment or mini-antibody derived from the inhibitor of the present invention. If desired, an effective daily dose of a pharmaceutical composition may be administered as two, three, four, five, six or more sub-doses administered separately at appropriate intervals throughout the day, optionally, in unit dosage forms. In some embodiments, the human monoclonal antibodies of the present invention are administered by slow continuous infusion over a long period, such as more than 24 hours, in order to minimize any unwanted side effects. An effective dose of a inhibitor of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of a inhibitor of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Antibodies of the Present Invention:

The first object of the present invention relates to a monoclonal antibody having binding specificity for the extracellular domain of CD38 which comprises:

a heavy chain comprising i) the H-CDR1 as set forth in SEQ ID NO:5, ii) the H-CDR2 as set forth in SEQ ID NO:6 and iii) the H-CDR3 as set forth in SEQ ID NO:7, and, a light chain comprising i) the L-CDR1 as set forth in SEQ ID NO:8, ii) the L-CDR2 as set forth in SEQ ID NO:9 and iii) the L-CDR3 as set forth in SEQ ID NO:10.

```
                                       SEQ ID NO: 5
     (H-CDR1): GYTFTSYW

SEQ ID NO: 6
     (H-CDR2): IYPGDGDT

SEQ ID NO: 7
     (H-CDR3): ARERTTGAPRYFDV

SEQ ID NO: 8
     (L-CDR1): ENIYSF
```

-continued (L-CDR2): NTK                                            SEQ ID NO: 9

(L-CDR3): QHHYGIPLT                                      SEQ ID NO: 10

In some embodiments, the monoclonal antibody of the present invention comprises a VH domain having at least 70% of identity with the amino acid sequence as set forth in SEQ ID NO:3.

In some embodiments, the monoclonal antibody of the present invention comprises a VL domain having at least 70% of identity with the amino acid sequence as set forth in SEQ ID NO:4.

According to the present invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence. According to the invention a first amino acid sequence having at least 90% of identity with a second amino acid sequence means that the first sequence has 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

The present invention thus provides antibodies comprising functional variants of the VL region, VH region, or one or more functional variants of the CDRs of BB51 antibody.

A functional variant of a VL, VH, or CDR used in the context of a monoclonal antibody of the present invention still allows the antibody to retain at least a substantial proportion (at least about 50%, 60%, 70%, 80%, 90%, 95% or more) of the affinity/avidity and/or the specificity/selectivity of the parent antibody (i.e. BB51 antibody antibody) and in some cases such a monoclonal antibody of the present invention may be associated with greater affinity, selectivity and/or specificity than the parent Ab. Such functional variants typically retain significant sequence identity to the parent Ab. The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements. The sequences of CDR variants may differ from the sequence of the CDRs of the parent antibody sequences through mostly conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected as follows:

Aliphatic residues I, L, V, and M
Cycloalkenyl-associated residues F, H, W, and Y
Hydrophobic residues A, C, F, G, H, I, L, M, R, T, V, W, and Y
Negatively charged residues D and E
Polar residues C, D, E, H, K, N, Q, R, S, and T
Positively charged residues H, K, and R
Small residues A, C, D, G, N, P, S, T, and V
Very small residues A, G, and S
Residues involved in turn A, C, D, E, G, H, K, N, Q, R, S, P, and formation T
Flexible residues Q, T, K, S, G, P, D, E, and R More conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of BB51 antibody. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 70% of identity to the parent peptide.

In some embodiments, the monoclonal antibody of the present invention is chimeric antibody. In some embodiments, the monoclonal antibody of the present invention is a chimeric antibody having a heavy chain as set forth in SEQ ID NO:3. In some embodiments, the monoclonal antibody is a chimeric antibody having a light chain as set forth in SEQ ID NO:4. In some embodiments, the monoclonal antibody of the present invention is a chimeric antibody having a heavy chain as set forth in SEQ ID NO:3 and a light chain as set forth in SEQ ID NO:4.

In some embodiments, the monoclonal antibody of the present invention is a humanized antibody.

The monoclonal antibody of the present invention can be characterized by one or more of the functional or structural features of the aspects described above, or by any combination of selected functional and structural features.

The antibody of the present invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a monoclonal antibody of the present invention may be switched by known methods. Typical, class switching techniques may be used to convert one IgG subclass to another, for instance from IgG1 to IgG2. Thus, the effector function of the human monoclonal antibodies of the present invention may be changed by isotype switching to, e.g., an IgG1, IgG2, IgG3, IgG4, IgD, IgA, IgE, or IgM antibody for various therapeutic uses. In some embodiments, the antibody of the present invention is a full-length antibody. In some embodiments, the full-length antibody is an IgG1 antibody. In some embodiments, the full-length antibody is an IgG4 antibody. In some embodiments, the IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys sequence. Other suitable stabilized IgG4 antibodies are disclosed in WO2008145142, which is hereby incorporated by reference in its entirety. In some embodiments, the monoclonal antibody of the present invention is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol. 75(24): 12161-12168 (2001).

In addition or alternative to modifications made within the framework or CDR regions, antibodies of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, a monoclonal antibody of the present invention may be chemically modified (e.g., one or more chemical moieties can be attached to the antibody) or be modified to alter its glycosylation, again to alter one or more functional properties of the antibody. For example, it will be appreciated that the affinity of antibodies provided by the present invention may be altered using any suitable method known in the art. The present invention therefore also relates to variants of the antibody molecules of the present invention, which have an improved affinity for CD38. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In some embodiments, one or more amino acid residues are altered to thereby alter the ability of the antibody to fix complement. This approach is described further in PCT Publication WO 94/29351 by Bodmer et al. In some embodiments, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcyRI, FcyRII, FcyRIII and FcRn have been mapped and variants with improved binding have been described (see Shields, R. L. et al, 2001 J. Biol. Chen. 276:6591-6604, WO2010106180).

In some embodiments, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the human monoclonal antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the human monoclonal antibodies of the present invention can be produced in yeasts or filamentous fungi engineered for mammalian-like glycosylation pattern and capable of producing antibodies lacking fucose as glycosylation pattern (see for example EP1297172B1).

In some embodiments, the antibody is an antigen-binding fragment. Antibody fragments can be obtained by conventional techniques, such as by fragmentation of full-length antibodies or by expression of nucleic acids encoding antibody fragments in recombinant cells (see, for instance Evans et al., J. Immunol. Meth. 184, 123-38 (1995)). The fragments can then be tested or screened for their properties in the same manner as described herein for full-length antibodies.

In some embodiments, the monoclonal antibody of the present invention is a scFv fragment comprising the VH and the VL domain of the antibody of the present invention. In some embodiments, the scFv fragment of the present invention consists of the amino acid sequence as set forth in SEQ ID NO:11.

```
>scEv antibody
                                    SEQ ID NO: 11
DIQMTQSPASLSASVGETVTITCRASENTYSFLAWYQQKQGKSPQLLVYN

TKTLTEGVPSRFSGSGSGTQFSLKINNLQPEDFGSYYCQHHYGIPLTFGA

GTKLELKGGGGSGGGGSGGGGSQVQLQQSGAELARPGASVKLSCKASGYT

FTSYWMQWVKQRPGQGLEWIGAIYPGDGDTRYTQKFKGKATLTADKSSST

AYMQLSNLTSEDSAVYYCARERTTGAPRYFDVWGAGTTVTSS
```

Nucleic Acid Molecules and Uses Thereof for Manufacturing the Antibodies of the Present Invention:

The monoclonal antibody of the present invention may be produced by any technique known in the art, such as, without limitation, any chemical, biological, genetic or enzymatic technique, either alone or in combination. For example, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, California) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the present invention relates to a nucleic acid sequence encoding a monoclonal antibody of the present invention. In some embodiments, the nucleic acid sequence encodes a heavy chain and/or a light chain of a monoclonal antibody of the present invention.

Typically, said nucleic acid is a DNA or RNA molecule, which may be included in any suitable vector. The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication-defective retroviruses, adenoviruses and adeno-associated viruses), which serve equivalent functions.

So, a further object of the present invention relates to a vector comprising a nucleic acid of the present invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a host cell which has been transfected, infected or transformed by a nucleic acid and/or a vector according to the present invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the present invention may be used to produce a monoclonal antibody of the present invention in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculo virus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G1 1.16Ag.20 cell (ATCC CRL1662, hereinafter referred to as "YB2/0 cell"), and the like.

The present invention also relates to a method of manufacturing a recombinant host cell expressing an antibody according to the present invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

Multispecific Antibodies of the Present Invention:

A further object of the present invention relates to a multispecific antibody comprising a first antigen binding site from a monoclonal antibody of the present invention and at least one second antigen binding site.

According to the invention the multispecific antibody of the present invention binds to an extracellular domain of CD38 and to an extracellular domain of another antigen of interest.

In some embodiments, the second antigen-binding site is used for recruiting a killing mechanism such as, for example, by binding an antigen on a human effector cell or by binding a cytotoxic agent or a second therapeutic agent.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radiolabeled peptides), chemotherapeutic agents and prodrugs.

In some embodiments, the second antigen binding site is used for recruiting T cells. In some embodiments, the second antigen binding site has specificity for the extracellular domain of CD3ε.

In some embodiments, the multispecific antibody of the present invention comprises an antigen-binding domain comprising, consisting of, or consisting essentially of, a single chain variable fragment (scFv) of the antibody of the present invention.

In some embodiments, the antigen binding domain comprises a linker peptide. The linker peptide may be positioned between the light chain variable region and the heavy chain variable region.

Exemplary formats for the multispecific antibody molecules of the present invention include, but are not limited to (i) two antibodies cross-linked by chemical heteroconjugation, one with a specificity to CD38 and another with a specificity to another antigen such as CD3ε; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivaient bispecific binding protein consisting of two identical Fab fragments linked to a different Fab fragment; (ix) a so-called Scorpion molecule, comprising, e.g., two scFvs fused to both termini of a human Fab-arm; and (x) a diabody.

Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies.

In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is a antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is a antibody of the present invention and the second antibody has a different binding specificity, or vice versa. The reducing conditions may, for example, be provided by adding a reducing agent, e.g. selected from 2-mercaptoethylamine, dithiothreitol and tris (2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. In some other embodiments, the bispecific antibody of the present invention is symmetric bispecific antibody of the class IgG4 comprising two heavy chains which each comprise a variable domain, CH1 domain and a hinge region, wherein in each heavy chain: the cysteine in the CH1 domain which forms an inter-chain disulphide bond with a cysteine in a light chain is substituted with another amino acid; and optionally one or more of the amino acids positioned in the upper hinge region is substituted with cysteine, wherein the constant region sequence of each heavy chain is similar or identical and the variable region in each heavy chain is different. Said bispecific format antibody is described in the international patent application WO2013124450. In some embodiments, the bispecific antibody of the present invention is an asymmetric antibody comprising two heavy chains or heavy chain fragments each comprising at least a variable region, a hinge region and a CH1 domain, wherein a first heavy chain or fragment thereof is of a class IgG4 and has a) the inter-chain cysteine at position 127, numbered according to the Kabat numbering system, in the CH1 domain is substituted with another amino acid; and b. optionally one or more of the amino acids positioned in the upper hinge region is substituted with cysteine, and wherein the second heavy chain or fragment thereof is characterised in that part or all of the chain has a different amino acid sequence to said first heavy chain in at least the region outside the variable region (for example the constant region). Said bispecific format antibody is described in the international patent application WO 2013124451.

In some embodiments, the multispecific antibody of the present invention is a Bi-specific T-cell engager (BiTE) antibody.

In some embodiments, the multispecific antibody of the present invention is a BITE® antibody.

In some embodiments, the multispecific antibody of the present invention comprises the sequence as set forth in SEQ IQ NO:12.

>Sequence of Bi38-3
SEQ ID NO: 12
DIQMTQSPASLSASVGETVTITCRASENTYSFLAWYQQKQGKSPQLLVYN

TKTLTEGVPSRFSGSGSGTQFSLKINNLQPEDFGSYYCQHHYGIPLTFGA

GTKLELKGGGGSGGGGSGGGGSQVQLQQSGAELARPGASVKLSCKASGYT

FTSYWMQWVKQRPGQGLEWIGAIYPGDGDTRYTQKFKGKATLTADKSSST

AYMQLSNLTSEDSAVYYCARERTTGAPRYFDVWGAGTTVTVSSGGGGSGG

GGSGGGGSDIKLQQSGAELARPGASVKMSCKASGYTFTRYTMHWVKQRPG

QGLEWIGYINPSRGYTNYNQKFKDKATLTTDKSSSTAYMQLSSLTSEDSA

VYYCARYYDDHYCLDYWGQGTTLTVSSGGGGSGGGGSGGGGSVDDIQLTQ

SPAIMSASPGEKVTMTCSASSSVSYMNWYQQKSGTSPKRWIYDTSKLASG

VPAHFRGSGSGTSYSLTISGMEAEDAATYYCQQWSSNPFTFGSGTKLELK

AAA

The invention also provides a nucleic acid encoding for a multispecific antibody of the present invention. In some embodiments, the nucleic acid is incorporated in a vector as such as described above.

Chimeric Antigen Receptors (CARs) and Uses Thereof for Manufacturing Host Cells that Express Said CARs:

The present invention also provides chimeric antigen receptors (CARs) comprising an antigen binding domain of the antibody of the present invention.

As used herein, the term "chimeric antigen receptor" or "CAR" has its general meaning in the art and refers to an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. Moreover, when expressed in T-cells, CARs advantageously do not dimerize with endogenous T cell receptor (TCR) alpha and beta chains. Typically, said chimeric antigen receptor comprises at least one VH and/or VL sequence of the antibody of the present invention. The chimeric antigen receptor the present invention also comprises an extracellular hinge domain, a transmembrane domain, and an intracellular T cell signaling domain.

In some embodiments, the antigen binding domain comprises a linker peptide. The linker peptide may be positioned between the light chain variable region and the heavy chain variable region.

In some embodiments, the invention provides CARs comprising an antigen-binding domain comprising, consisting of, or consisting essentially of, a single chain variable fragment (scFv) of the antibody of the present invention.

In some embodiments, the CAR of the present invention consists of the amino acid sequence as set forth in SEQ ID NO:13 or SEQ ID NO:14.

Thus, a further object of the present invention relates to a host cell engineered to express a chimeric antigen receptor (CAR) as above described.

In some embodiments, the host cell is a cytotoxic lymphocyte.

As used herein, the term "cytotoxic lymphocytes" has its general meaning in the art and refers to lymphocytes targeting destruction of intracellular pathogens, such as viral agents, in which a lethal hit delivered to infected target cells is required to limit spread of infection. According to the invention, the "cytotoxic lymphocytes" includes cytotoxic T cell and natural killer cell.

In some embodiments, the host cell is natural killer cell.

```
CAR CD38 1G
                                                               SEQ ID NO: 13
DIQMTQSPASLSASVGETVTITCRASENIYSFLAWYQQKQGKSPQLLVYNTKTLTEGVPSRFSGSGSGT

QFSLKINNLQPEDFGSYYCQHHYGIPLTFGAGTKLELKGGGGSGGGGSGGGGSQVQLQQSGAELARPGA

SVKLSCKASGYTFTSYWMQWVKQRPGQGLEWIGAIYPGDGDTRYTQKFKGKATLTADKSSSTAYMQLSN

LTSEDSAVYYCARERTTGAPRYFDVWGAGTTVTVSSLEHFVPVFLPAKPTTTPAPRPPTPAPTIASQPL

SLRPEACRPAAGGAVHTRGLDFACDIYIWAPLAGTCGVLLLSLVITLYCNHRNRVKFSRSADAPAYQQG

QNQLYNELNLGRREEYDVLDKRRGRDPEMGGKPQRRKNPQEGLYNELQKDKMAEAYSEIGMKGERRRGK

GHDGLYQGLSTATKDTYDALHMQALPPR

CAR CD38 3G
                                                               SEQ ID NO: 14
DIQMTQSPASLSASVGETVTITCRASENIYSFLAWYQQKQGKQGKSPQLLVYNTKTLTEGVPSRFSGSGSGT

QFSLKINNLQPEDFGSYYCQHHYGIPLTFGAGTKLELKGGGGSGGGGSGGGGSQVQLQQSGAELARPGA

SVKLSCKASGYTFTSYWMQWVKQRPGQGGLEWIGAIYPGDGDTRYTQKFKGKATLTADKSSSTAYMQLSN

LTSEDSAVYYCARERTTGAPRYFDVWGAGTTVTVSSLEIEVMYPPPYLDNEKSNGTIIHVKGKHLCPSP

LFPGPSKFWVLVVVGGVLACYSLLVTVAFIIFWVRSKRSRLLHSDYMNMTPRRPGPTRKHYQPYAPPR

DFAAYRSKRGRKKLLYIFKQPFMRPVQTTQEEDGCSCRFPEEEEGGCELGSRVKFSRSADAPAYQQGQN

QLYNELNLGRREEYDVLDKRRGRDPEMGGSPRRKNPQEGLYNELQKDKMAEAYSEIGMKGERRRGKGGHD

GLYQGLSTATKDTYDALHMQALPPR
```

In some embodiments, the CAR comprises an extracellular hinge domain, a transmembrane domain, and an intracellular T cell signaling domain selected from the group consisting of CD28, 4-1BB, and CD3ζ intracellular domains. CD28 is a T cell marker important in T cell co-stimulation. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

In some embodiments, the chimeric antigen receptor of the present invention can be glycosylated, amidated, carboxylated, phosphorylated, esterified, N-acylated, cyclized via, e.g., a disulfide bridge, or converted into an acid addition salt and/or optionally dimerized or polymerized.

The invention also provides a nucleic acid encoding for a chimeric antigen receptor of the present invention. In some embodiments, the nucleic acid is incorporated in a vector as such as described above.

As used herein, the term "natural killer cell" has its general meaning in the art and refers to a type of cytotoxic lymphocyte critical to the innate immune system. The role of NK cells is analogous to that of cytotoxic T cells in the vertebrate adaptive immune response. NK cells provide rapid responses to virus-infected cells and respond to tumor formation.

In some embodiments, the host cell is a T cell, e.g. isolated from peripheral blood lymphocytes (PBL) or peripheral blood mononuclear cells (PBMC). In some embodiments, the T cell can be any T cell, such as a cultured T cell, e.g., a primary T cell, or a T cell from a cultured T cell line, e.g., Jurkat, SupTl, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, CD4+/CD8+ double positive T cells, CD4+ helper T cells, e.g., Th2 cells, CD8+ T cells (e.g., cytotoxic T cells), tumor infiltrating cells, memory T cells, naive T cells, and the like. The T cell may be a CD8+ T cell or a CD4+ T cell.

Thus a further object of the present invention is a CAR-T cells comprising the chimeric antigen receptor (CAR) of the invention.

In some embodiments, the host cell is a pluripotent stem cell (PSC). PSCs can be indeed be modified by a CAR and then can be used for deriving T cells (e.g. WO 2017100403). PSCs include embryonic stem cell (ESCs) and induced pluripotent stem cell (iPSCs). iPSCs can be generated directly from adult cells (e.g., somatic cells). iPSCs can be typically derived or generated by introducing a specific set of pluripotency-associated genes, or "reprogramming factors", into a given cell type. Reprogramming factors include, but are not limited to, OCT4 (also known as "POU5FL"), SOX2, cMYC, and KLF4, which are also known as Yamanaka factors. See Takahashi, K; Yamanaka, S (2006). "Induction of pluripotent stem cells from mouse embryonic and adult fibroblast cultures by defined factors". Cell 126 (4): 663-76.

In some embodiments, the host cell is a hematopoietic stem cell. As used herein, the term "hematopoietic stem cell" or "HSC" refers to blood cells that have the capacity to self-renew and to differentiate into precursors of blood cells. These precursor cells are immature blood cells that cannot self-renew and must differentiate into mature blood cells. Hematopoietic stem progenitor cells display a number of phenotypes, such as Lin-CD34+CD38–CD90+CD45RA–, Lin-CD34+CD38–CD90–CD45RA–, Lin-CD34+CD38+IL-3aloCD45RA–, and Lin-CD34+CD38+CD10+ (Daley et al., Focus 18:62-67, 1996; Pimentel, E., Ed., Handbook of Growth Factors Vol. III: Hematopoietic Growth Factors and Cytokines, pp. 1-2, CRC Press, Boca Raton, Fla., 1994). Within the bone marrow microenvironment, the stem cells self-renew and maintain continuous production of hematopoietic stem cells that give rise to all mature blood cells throughout life. In some embodiments, the hematopoietic progenitor cells or hematopoietic stem cells are isolated form peripheral blood cells.

In some embodiments, the CAR activity can be controlled if desirable to optimize the safety and efficacy of a CAR therapy. There are many ways CAR activities can be regulated. For example, inducible apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention.

Methods of Treatment and Pharmaceutical Compositions:

The antibodies, the multispecific antibodies and the CAR-T cells of the present invention are particularly suitable for use in therapy.

Thus a further object of the present invention relates to a method of therapy in a subject in need thereof comprising administering to the subject a therapeutically effective amount of the antibody of the present invention and/or the multispecific antibody of the present invention and/or the population of CAR-T cells of the present invention.

In particular, the multispecific antibodies and the CAR-T cells of the present invention are particularly suitable for the treatment of cancer and more particularly for the treatment of CD38-positive hematological malignancies.

Thus, the present invention relates to the antibody of the present invention and/or the multispecific antibody of the present invention and/or the population of CAR-T cells of the present invention for use for the treatment of cancer in a subject in need thereof.

In some embodiment, the cancer is CD38-positive cancer.

In some embodiments, the CD38-positive cancer is CD38-positive hematological malignancy.

In some embodiment, the CD38-positive hematological malignancy is multiple myeloma.

In some embodiment, the cancer is a cancer expressing no or very low B-cell maturation antigen (BCMA) levels In some embodiment, the cancer is CD38-positive cancer expressing no or very low B-cell maturation antigen (BCMA) levels.

In some embodiment, the cancer is CD38-positive hematological malignancy expressing no or very low B-cell maturation antigen (BCMA) levels.

In some embodiments, the multispecific antibody of the present invention and/or the population of CAR-T cells of the present invention triggers specific T-cell mediated lysis of CD38-positive cancer.

In some embodiments, the multispecific antibody of the present invention and/or the population of CAR-T cells of the present invention triggers specific T-cell mediated lysis of CD38-positive cancer while preserving B cells and NK cells from T cell cytotoxic activity.

As used herein, the term "subject" refers to any mammals, such as a rodent, a feline, a canine, and a primate. Particularly, in the present invention, the subject is a human afflicted with or susceptible to be afflicted with a cancer, preferably a CD38-positive cancer, and more preferably CD38-positive hematological malignancy.

In some embodiment, the subject suffer from relapse of cancer. In some embodiment, the subject suffer from relapse of CD38-positive cancer. In some embodiment, the subject suffer from relapse of CD38-positive hematological malignancy.

In some embodiment, the subject have resistance to monoclonal antibodies targeting CD38 (such as daratumumab).

In some embodiment, the subject have undergone a therapy with monoclonal antibodies targeting CD38 and have acquired resistance to anti-CD38 monoclonal antibodies.

In a particular embodiment, antibody of the present invention and/or the multispecific antibody of the present invention and/or the population of CAR-T cells of the present invention may be used in combination with anti-cancer therapy.

Thus, the invention refers to a method of therapy in a subject in need thereof comprising administering to the subject a therapeutically effective amount of the antibody of the present invention and/or the multispecific antibody of the present invention and/or the population of CAR-T cells of the present invention, and ii) a classical treatment, as a combined preparation for treating cancer.

As used herein, the term "anti-cancer therapy" has its general meaning in the art and refers to any compound, natural or synthetic, used for the treatment of cancer.

In a particular embodiment, anti-cancer therapy refers to radiation therapy, antibody therapy or chemotherapy.

As used herein, the term "chemotherapeutic agent" refers to chemical compounds that are effective in inhibiting tumor growth. Examples of chemotherapeutic agents include multkinase inhibitors such as sorafenib and sunitinib, alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33: 183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defo famine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisp latin and carbop latin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

As used herein, the term "radiation therapy" has its general meaning in the art and refers the treatment of cancer with ionizing radiation. Ionizing radiation deposits energy that injures or destroys cells in the area being treated (the target tissue) by damaging their genetic material, making it impossible for these cells to continue to grow. One type of radiation therapy commonly used involves photons, e.g. X-rays. Depending on the amount of energy they possess, the rays can be used to destroy cancer cells on the surface of or deeper in the body. The higher the energy of the x-ray beam, the deeper the x-rays can go into the target tissue. Linear accelerators and betatrons produce x-rays of increasingly greater energy. The use of machines to focus radiation (such as x-rays) on a cancer site is called external beam radiation therapy. Gamma rays are another form of photons used in radiation therapy. Gamma rays are produced spontaneously as certain elements (such as radium, uranium, and cobalt 60) release radiation as they decompose, or decay. In some embodiments, the radiation therapy is external radiation therapy. Examples of external radiation therapy include, but are not limited to, conventional external beam radiation therapy; three-dimensional conformal radiation therapy (3D-CRT), which delivers shaped beams to closely fit the shape of a tumor from different directions; intensity modulated radiation therapy (IMRT), e.g., helical tomotherapy, which shapes the radiation beams to closely fit the shape of a tumor and also alters the radiation dose according to the shape of the tumor; conformal proton beam radiation therapy; image-guided radiation therapy (IGRT), which combines scanning and radiation technologies to provide real time images of a tumor to guide the radiation treatment; intraoperative radiation therapy (IORT), which delivers radiation directly to a tumor during surgery; stereotactic radiosurgery, which delivers a large, precise radiation dose to a small tumor area in a single session; hyperfractionated radiation therapy, e.g., continuous hyperfractionated accelerated radiation therapy (CHART), in which more than one treatment (fraction) of radiation therapy are given to a subject per day; and hypofractionated radiation therapy, in which larger doses of radiation therapy per fraction is given but fewer fractions.

As used herein, the term "immune checkpoint inhibitor" refers to molecules that totally or partially reduce, inhibit, interfere with or modulate one or more immune checkpoint proteins.

As used herein, the term "immune checkpoint protein" has its general meaning in the art and refers to a molecule that is expressed by T cells in that either turn up a signal (stimulatory checkpoint molecules) or turn down a signal (inhibitory checkpoint molecules).

Examples of stimulatory checkpoint include CD27 CD28 CD40, CD122, CD137, OX40, GITR, and ICOS. Examples of inhibitory checkpoint molecules include A2AR, B7-H3, B7-H4, BTLA, CTLA-4, CD277, IDO, KIR, PD-1, PD-L1, LAG-3, TIM-3 and VISTA.

As used herein, the terms "combined treatment", "combined therapy" or "therapy combination" refer to a treatment that uses more than one medication. The combined therapy may be dual therapy or bi-therapy.

The medications used in the combined treatment according to the invention are administered to the subject simultaneously, separately or sequentially.

As used herein, the term "administration simultaneously" refers to administration of 2 active ingredients by the same route and at the same time or at substantially the same time. The term "administration separately" refers to an administration of 2 active ingredients at the same time or at substantially the same time by different routes. The term "administration sequentially" refers to an administration of 2 active ingredients at different times, the administration route being identical or different In particular, the population of CAR-T cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. Currently, most adoptive immunotherapies are autolymphocyte therapies (ALT) directed to treatments using the patient's own immune cells. These therapies involve processing the patient's own lymphocytes. Typically, the treatments are accomplished by removing the patient's lymphocytes and transforming said cells in the population of CAR-T cells as above described. Once the CAR-T cells are prepared with the CAR of the present invention, these ex vivo cells are reinfused into the patient to enhance the immune system to kill tumor calls. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the T cells with the desired specificity, on the age and weight of the recipient, on the severity of the targeted condition and on the immunogenicity of the targeted Ags. These amount of cells can be as low as approximately $10^3$/kg, preferably $5 \times 10^3$/kg; and as high as $10^7$/kg, preferably $10^8$/kg. The number of cells will depend upon the ultimate use for which the composition is intended, as will the type of cells included therein. For example, if cells that are specific for a particular Ag are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

For administration, the antibody of the present invention is formulated as a pharmaceutical composition. A pharmaceutical composition comprising the antibody of the present invention can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc. The form of the pharmaceutical compositions, the route of administration, the dosage and the regimen naturally depend upon the condition to be treated, the severity of the illness, the age, weight, and sex of the patient, etc. The pharmaceutical compositions of the invention can be formulated for a topical, oral, parenteral, intranasal, intravenous, intramuscular, subcutaneous or intraocular administration and the like.

Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In some embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention will be further illustrated by the following figures and examples. However, these examples and figures should not be interpreted in any way as limiting the scope of the present invention.

FIGURES

FIG. 1. Bi38-3 dose dependent autologous T cell-mediated lysis of MM tumor cells from patients. CD138+ plasma cells were purified from the bone marrow of the patients and co-cultured with autologous CD3+ T cells isolated from PBMC at an E:T cell ratio of 5:1 for 24 hours. Cultures were analyzed by FACS to monitor the number of CD138+ cells falling into the live gate. Shown are the mean from triplicate experiments indicating the percentages of live CD138+ cells (relative to the untreated condition) in 4 different patients at diagnosis and 3 at relapse. Histograms show the average effects of Bi38-3 alone, T cells alone and T cells with Bi38-3 (100 ng/mL) on tumor plasma cells form the same 5 patients at diagnosis (upper) and 3 at relapse (lower). Standard deviations are shown and p values were calculated with a Student's t test ($*p<0.05$; $p<0.01$; $*p<0.001$).

Figure 2:
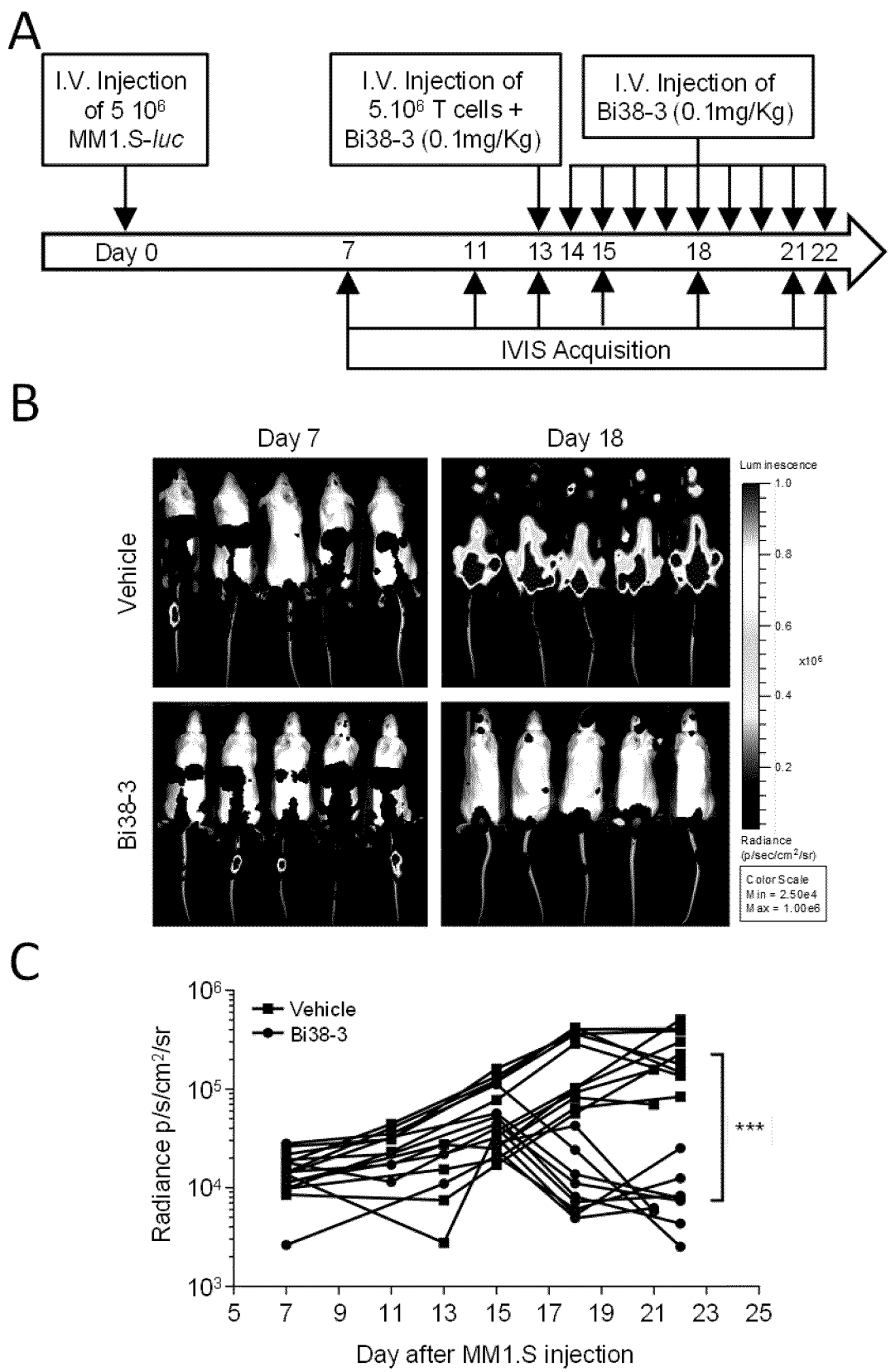

FIG. 2. In Vivo Activity of Bi38-3 in the MM1.Sluc Xenograft mouse model. A. Treatment schedule. NSG mice were inoculated with $5 \cdot 10^6$ MM1.SLuc cells (i.v) and treatment was initiated at day 13 when similar levels of luciferase expressing MM cells were detected in all mice. Purified T cells were ($5 \cdot 10^6$ cells/mouse) were infused i.v., together with Bi38-3 or PBS (blue arrows). Injections of Bi38-3 (0.1 mg/Kg) i.v. were repeated daily for 9 days (black arrows). Luciferase activity was measured with the IVIS Imaging System at 7, 11, 13, 15, 18 and 21 (or 22) days after tumor injection (red arrows). B. Serial bioluminescence imaging to assess myeloma progression/regression. Radiance was measured on the entire body of mice. Images on the left indicate luminescence at 7 days after inoculation with MM.1S myeloma cells and before the beginning of the treatment. Images on the right indicate 18 days after inoculation with MM.1S cells and 4 days after treatment with Bi38-3 (upper panel) or with vehicle (lower panel). The radiance color scale is represented on the right. C. Longitudinal radiance levels of vehicle (blue lines) and Bi38-3 (red lines) treated mice. Represents 9 mice per group inoculated with T cells from 2 independent donors. The p value was calculated at 22 days with a Student t test. ($***p<0.001$).

Figure 3:
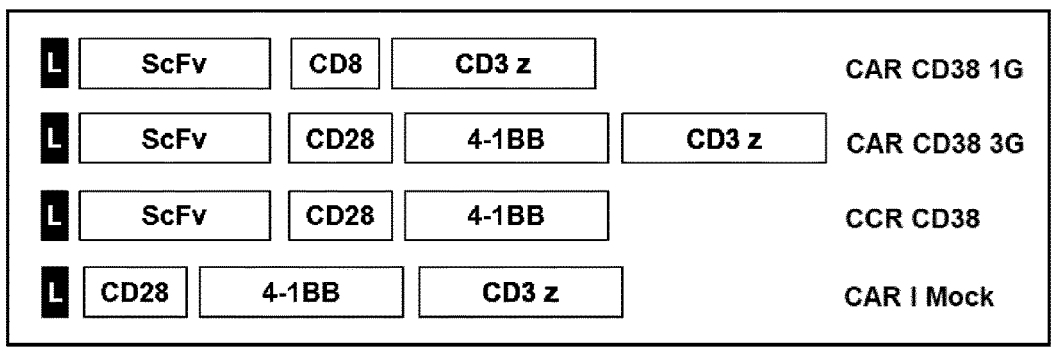
Figure 3:
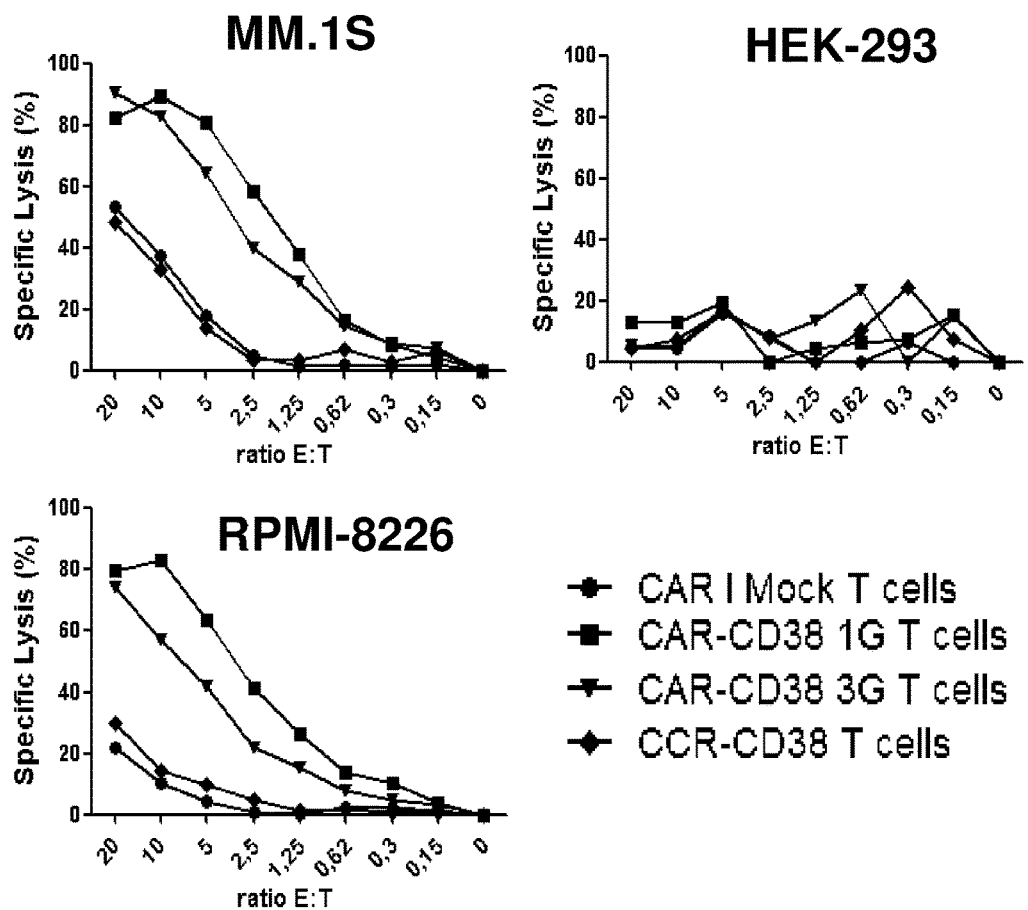

FIG. 3. In Vitro Activity of anti-CD38 CAR-T cells. A. Schematic representation of the structures of the different Chimeric Antigen Receptors (CAR) and co-stimulatory receptors (CCR). First generation (1G) CAR contains the CD3ζ signaling domain, 3rd generation CAR (3G) contains CD28, 4-1BB and CD3z signaling domains. CCR contains CD28 and 4-1BB signaling domains, but lacks the CD3ζ domain. The CAR Mock is devoid of the anti-CD38 scFv region. B. Cytotoxic activity of the different CAR-T on CD38 expressing MM (MM.1S and RPMI8226) and CD38 negative fibroblastic (HEK293) cells lines in vitro. Cells expressing the luciferase have been cultured for 20 h with the indicated CAR-T cells at various effector/target ratios (E:T). The cytotoxic activity was determined by measuring the level of luciferase in the culture. Representative of 4 independent experiments.

Figure 4A:
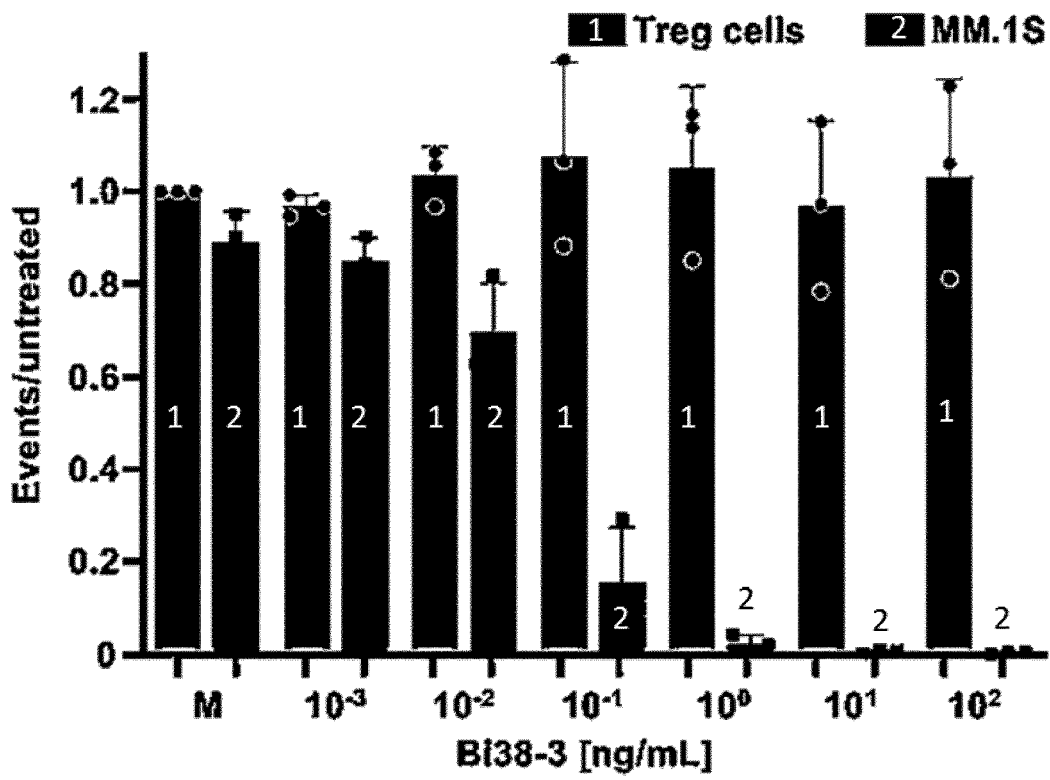
Figure 4B:
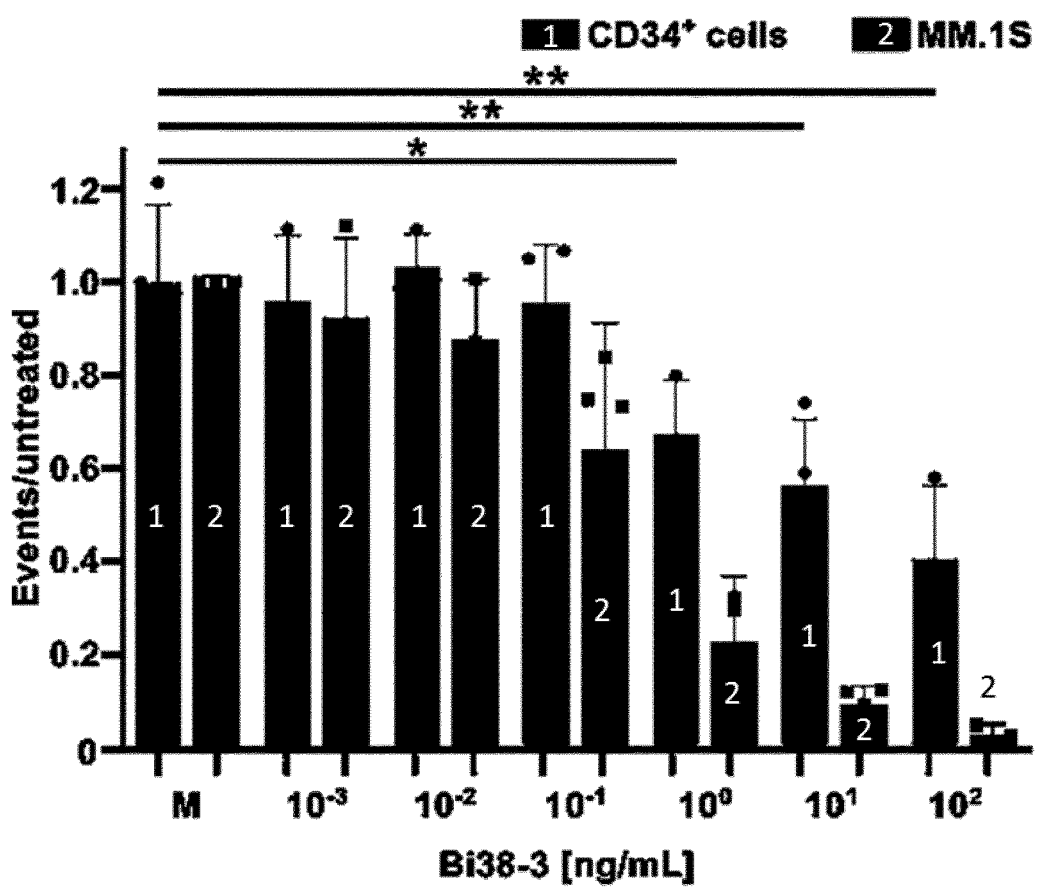

FIG. 4: Sensitivity of blood cells and bone marrow hematopoietic progenitors to Bi38-3. A. Relative Bi38-3 mediated T cell lysis of Treg versus MM1.S cells. Purified T cells from healthy donors (n=3) were co-cultured with increasing concentrations of Bi38-3 for 24 hours in the presence of MM1.S cells. B. Relative Bi38-3 mediated T cell lysis of CD34+ bone marrow hematopoietic progenitors versus MM1.S cells. Paired CD34+ hematopoietic progenitors and T cells purified from the bone marrow of healthy donors (hip surgery) (n=4) were co-cultured with increasing concentrations of Bi38-3 for 24 hours in the presence of MM1.S cells. The numbers of live CD20+ (B cells), FoxP3+ (Treg cells), CD34+ (Hematopoietic progenitors) and CD138+ (MM1.S cells) were calculated by FACS using counting beads and expressed as a ratio to untreated controls, respectively. Histograms show the ratios of B, Treg, CD34+ hematopoietic progenitor and MM.1S cells for each Bi38-3 concentrations and error bars indicate the SD. The normality of the CD34+ populations was established with a Shapiro-Wilk normality test and P-values were determined by an unpaired Student's t test (*$p<0.05$; $p<0.01$; *$p<0.001$).

EXAMPLE 1: A NOVEL CD38/CD3 BISPECIFIC T-CELL ENGAGER FOR THE TREATMENT OF MULTIPLE MYELOMA

Methods:
Construction and Purification of Bi38-3.

Bi38-3 was generated by the fusion of two scFvs derived from mouse hybridomas producing anti-human CD38 and CD3ε (BB51 and OKT3, respectively), linked by a 15-amino-acid glycine-serine (G4S1×3) spacer. The human CD8 leader peptide was genetically linked to the N-terminus of the fusion fragment and Myc-tag and His-tag sequences were introduced at the C-terminus. The sequence encoding for Bi38-3 was cloned into the pCDNA3 expression vector (ThermoFisher), and confirmed by sequencing. This vector was transiently transfected in HEK-293T cells and a protein of 55.6 Kd corresponding to Bi38-3 was purified from the supernatant using HisTrap HP columns (GE). The integrity of Bi38-3 was analyzed by Coomassie blue staining and western blot with an anti-Myc-tag antibody.

Cell Lines

MM1.S, NCI-H929 and KMS-11 MM cell lines were maintained in RPMI 1640 medium supplemented with 10% heat-inactivated fetal bovine serum, 100 units/mL penicillin, 10 μg/mL streptomycin, and 2 mM L-glutamine. All cell lines were monitored for mycoplasma contamination. Luciferase expressing MM1.S and KMS-11 cells (KMS11luc and MM1.Sluc) were generated by lentiviral transduction with a luciferase expressing vector (Addgene, pLenti CMV Puro LUC (w168-1) a gift from Eric Campeau & Paul Kaufman). To generate CD38 deficient MM1.S cells, two pairs of RNAs guides were designed to delete exons 2 and 3 of the CD38 gene. Annealed oligonucleotides were cloned into the pX458 vector (Addgene plasmid ID 48138, a gift from Dr Feng Zhang) and verified by sequencing. For Cas9 deletion, $2 \times 10^6$ MM1.Sluc cells were nucleofected with 2 μg of each Cas9 vector using Nucleofector-II (Lonza), incubated in culture medium for 24 h, FACS sorted for GFP positive cells and cloned in 96-well plates. Subclones were analyzed for CD38 expression by flow cytometry and CD38 negative clones were selected for further analysis.

Blood and Bone Marrow Samples

Peripheral blood samples from healthy donors were obtained from the Etablissement Francais du Sang (EFS). Fresh tumor plasma cells were collected from buffy coat of bone marrow aspirates from myeloma patients and further purified using anti-CD138 coated beads (Miltenyi). In all cases, informed consent of patients and volunteers were obtained in accordance with the Declaration of Helsinki and with approval of the Saint-Louis Hospital Internal Review Board.

Flow Cytometry and Cytotoxicity

To determine lysis of KMS-11luc or MM1Sluc MINI cell lines, purified peripheral T cells (effector) were incubated in culture medium (RPMI, 10% heat-inactivated fetal bovine serum, 100 units/mL penicillin, 10 μg/mL streptomycin, and 2 mM L-glutamine) with luciferase expressing MM1.S or KMS-11 cells (target) with an effector to target ratio of 1:5 in flat-bottomed 96 wells with various concentrations of Bi38-3. The luciferase signal produced by surviving MM cells was determined after 24 h using a CLARIOstar Plus luminometer plate reader (BMG LABTECH GmbH, Ortenberg, Germany) within 20 min after the addition of firefly luciferase substrate according to the manufacturer's instructions (Bright-Glo™ Luciferase assay System, Promega). T cell cytotoxicity on primary cells was assayed by flow cytometry using similar co-culture conditions. Effector T cells were co-incubated with purified target MM cells and serial dilutions of Bi38-3. After incubation, anti-human CD138-Allophycocyanin (APC) (clone 44F9—Miltenyi Biotec), anti-CD20-Brilliant Violet (BV) 605 (Clone 2H7—BioLegend), anti-CD4-APC/Cyanine 7 (Clone RPA-T4—BioLegend) and anti-CD8-BV421 (Clone RPA-T8—BioLegend) antibodies were added to the cells to distinguish target from effector cells and the numbers of live cells were determined using Brightcount beads (ThermoFisher) by flow cytometry. All FACS acquisition was performed on a Canto II (Beckon Dickinson). Analysis and calculation of proliferation indices were performed with Flowjo.

T Cell Activation and Proliferation Assays

For detection of activation, effector (T cells) and targets (MM1.S) cells were co-cultured at a ratio of 5:1 for 24 h, stained with anti-human CD4-APC-Cyanine 7 (Clone RPA-T4), anti-CD8-BV421 (Clone RPA-T8), anti-CD25-Phycoerythrin (Pe)/Cyanine 5 (clone BC96) and anti-CD69-BV711 (clone FN 50) antibodies (all from Biolegend) and analyzed by flow cytometry. For analysis of proliferation, T cells were labeled with CellTrace Violet dye (ThermoFisher) and subjected to stimulation with MM1.S cells or MM1.S-CD38KO with (or without) Bi38-3 (10 ng/mL) for 96 hours. Cells were stained with anti-CD4-APC/Cy7 (clone RPA-T4) and anti-CD8-BV421 (clone RPA-T8) antibodies, and analyzed by flow cytometry.

Quantification of Cytokines in Cell Culture Supernatants

The concentration of cytokines in supernatants from cytotoxicity assays were analyzed using the BD™ CBA Human Th1/Th2 Cytokine Kit II (Beckon Dickinson). Data were acquired on a Canto II and analyzed with the FCAP Array™ software (Beckon Dickinson).

Mouse Systemic Tumor Model

We used 6- to 12-week-old NOD/SCID/IL-2Rγnull mice (The Jackson Laboratory), under a protocol approved by the Institutional Animal Care and Use Committee (Comite d'éthique Paris-Nord). Mice were inoculated with 5×10⁶ MM1.Sluc cells by tail vein injection, followed, 14 days later, by infusion of 5×10⁶ purified human T cells (purified using Pan T-cell isolation kits from Miltenyi Biotec) containing (or not) Bi38-3 at 0.08 mg/Kg. Tail vein injection of Bi38-3 (or PBS for controls) was repeated daily for 9 days. No randomization or blinding methods were used. Bioluminescence imaging was performed every 3 or 4 days. Mice were injected intraperitoneally with 240 μL of D-Luciferin (15 mg/mL) (XenoLight D-Luciferin Potassium Salt, Perkin Elmer) and image acquisition was performed after 15 minutes using the IVIS Imaging System (PerkinElmer) with the Living Image software (PerkinElmer) on a 25-cm field of view at medium binning level and at various exposure times. Twenty-two days after inoculation of MM cells, all mice were sacrificed.

Results:

Construction, Production and Binding Properties of Bi38-3

Bi38-3 consists of two scFvs derived from mouse hybridomas, producing anti-human CD38 and CD3ε (BB51 and OKT3, respectively), linked by a 15-amino-acid glycine-serine (G4S1×3) spacer (not shown). Amino acid sequences corresponding to anti-CD38 heavy and light chains variable domains, of anti CD38 scFv as well as of Bi38-3 are depicted in Table 1.

TABLE 1

Amino acid sequences of Immunoglobulin (IgH and Igk) from the BB515 Hybridoma (anti-CD38), of the corresponding scFv and of Bi38-3.

| | | |
|---|---|---|
| Igk Vk12.44-Jk5: | DIQMTQSPASLSASVGETVTITCRASENIYSFLAWYQ QKQGKSPQLLVYNTKTLTEGVPSRFSGSGSGTQFSLK INNLQPEDFGSYYCQHHYGIPLTFGAGTKLELK (SEQ ID NO: 4) | Igk CDR1:ENIYSF (SEQ ID NO: 8)<br>Igk CDR2:NTK (SEQ ID NO: 9)<br>Igk CDR3:QHHYGIPLT (SEQ ID NO: 10) |
| IgH VH1.87-D1.1-J1 | QVQLQQSGAELARPGASVKLSCKASGYTFTSYWMQWV KQRPGQGLEWIGAIYPGDGDTRYTQKFKGKATLTADK SSSTAYMQLSNLTSEDSAVYYCARERTTGAPRYFDVW GAGTTVTVSS (SEQ ID NO: 3) | IgH CDR1:GYTFTSYW (SEQ ID NO: 5)<br>IgH CDR2:IYPGDGDT (SEQ ID NO: 6)<br>IgH CDR3: ARERTTGAPRYFDV (SEQ ID NO: 7) |
| Anti-CD38 scFv | MALPVTALLLPLALLLHAARPDIQMTQSPASLSASVG ETVTITCRASENIYSFLAWYQQKQGKSPQLLVYNTKT LTEGVPSRFSGSGSGTQFSLKINNLQPEDFGSYYCQH HYGIPLTFGAGTKLELKGGGGSGGGGSGGGGSQVQLQ QSGAELARPGASVKLSCKASGYTFTSYWMQWVKQRPG QGLEWIGAIYPGDGDTRYTQKFKGKATLTADKSSSTA YMQLSNLTSEDSAVYYCARERTTGAPRYFDVWGAGTT VTVSS (SEQ ID NO: 20) | Leader CD8a: MALPVTALLLPLALLLHAARP (SEQ ID NO: 19) |
| Bi38-3 | *MALPVTALLLPLALLLHAARP*DIQMTQSPASLSASVG ETVTITCRASENIYSFLAWYQQKQGKSPQLLVYNTKT LTEGVPSRFSGSGSGTQFSLKINNLQPEDFGSYYCQH HYGIPLTFGAGTKLELKGGGGSGGGGSGGGGSQVQLQ QSGAELARPGASVKLSCKASGYTFTSYWMQWVKQRPG QGLEWIGAIYPGDGDTRYTQKFKGKATLTADKSSSTA YMQLSNLTSEDSAVYYCARERTTGAPRYFDVWGAGTT VTVSSGGGGSGGGGSGGGGSDIKLQQSGAELARPGAS VKMSCKASGYTFTRYTMHWVKQRPGQGLEWIGYINPS RGYTNYNQKFKDKATLTTDKSSSTAYMQLSSLTSEDS AVYYCARYYDDHYCLDYWGQGTTLTVSSGGGGSGGGG SGGGGSVDDIQLTQSPAIMSASPGEKVTMTCSASSSV SYMNWYQQKSGTSPKRWIYDTSKLASGVPAHFRGSGS GTSYSLTISGMEAEDAATYYCQQWSSNPFTFGSGTKL ELKAAAEQKLISEEDLNGAVEHHHHHH (SEQ ID NO: 15) | Leader CD8a-scFv anti CD38-scFv anti CD3ε-Myc-Tag-His tag |

The anti-CD38 scFv was positioned N-terminally, the anti-CD3ε scFv C-terminally and followed by Myc-Tag and His×6-Tag sequences (not shown). Western blot analysis of HEK-293 cells transiently transfected with a Bi38-3 expression vector revealed a unique protein recognized by the anti-Myc-Tag antibody with the expected size of 55.6 Kd (data not shown). Bi38-3 was purified from culture supernatants of transiently transfected HEK-293 cells with His-Trap HP columns (GE). Purity of monomeric Bi38-3 protein was demonstrated by gel electrophoresis followed by Coomassie Blue staining (data not shown). Binding of Bi38-3 to CD38 expressing MM1.S, KMS11 and NCI-H939 MM cells was analyzed by flow cytometry with an anti-Fab antibody that recognizes the scFv domains. We observed that Bi38-3 was detected at the surface of MM cell lines, with a less intense staining of KMS11 cells that express lower levels of CD38, and stronger signals on MM1.S and NCI-H929 cells that display higher levels of CD38 (data not shown). To verify the specificity of Bi38-3 to CD38, we used a CRISPR/Cas9 approach to inactivate the CD38 gene in MM1.S cells (MM1.S-KO) (data not shown). FACS analysis revealed that Bi38-3 could not be detected at the surface of CD38 negative MM1.S-KO cells (data not shown). Thus, purified Bi38-3 efficiently and specifically recognizes CD38 on MM cells.

Bi38-3 Induces T-Cell Activation and Proliferation in Response to MM Cells In Vitro We next investigated the T cell responses to MM cells triggered by Bi38-3. First, we performed FACS analysis to measure the proliferation index of violet fluorescent stained T cells. Stimulation of donor effector T cells (E) with Bi38-3 in the presence MM1.S target cells (T) led to robust proliferation, with an average of 5 cell divisions (expansion index) after 4 days, a level slightly higher than induced by treatment with anti-CD3/CD28 beads (data not shown). Proliferation required CD38 expression on target cells, as T lymphocytes cultured with CD38-deficient MM1.S cells and Bi38-3 did not proliferate. Furthermore, neither culture with Bi38-3 alone nor MM1.S cells alone induced significant T cell expansion.

Second, we analyzed the expression of CD69 and CD25 early activation markers on donor T cells. Following overnight co-culture with MM1.S cells, CD4 and CD8 T cells readily upregulated both markers in a Bi38-3 dose dependent manner, with up to 80% CD69 positive T cells detected at the highest concentrations (data not shown). In contrast, we observed a weaker percentage of CD25 and CD69 expressing T cells (15% and 30% respectively) upon stimulation with 100 ng/mL of Bi38-3 alone. Furthermore, co-culture with MM1.S target cells alone did not induce expression of activation markers (data not shown). In line with this, co-culture with MM1.SKO cells and Bi38-3 trigger a lower induction of CD69 and CD25 compared to co-cultures with wild type MM1.S cells (data not shown), demonstrating that upregulation of activation markers was enhanced by CD38 expression on target cells Last, we monitored the production of cytokines triggered by Bi3 8-3. Co-culture of donor T cells with MM1.S triggered production of Interferon-gamma (IFNg), Tumor necrosis factor-alpha (TNFa), Interleukine-2 (IL-2), IL-4 and IL-10 in a Bi38-3 dose dependent manner (data not shown). In contrast, stimulation with Bi38-3 alone or co-culture with MM1.S alone could not induce T cell secretion of any of these cytokines (not shown). Altogether, these results indicate that Bi38-3 directs T cell proliferation, activation and cytokine release in response to CD38 expressing MM cells in vitro.

Bi38-3 Induces CD38-Dependent T-Cell Mediated Killing of MM Cells In Vitro

To assess the function of Bi38-3, we performed co-culture assays to measure the cytotoxic activity of effector T cells, isolated from PBMC of healthy donors, on firefly luciferase expressing target KMS11 and MM1.S MM cell lines. The levels of luciferase, which indicate the number of live MM target cells remaining, were compared to the luciferase observed in untreated controls in order to determine the percentages of killing in the presence of various concentrations of Bi38-3. T cells readily killed KMS11 target cells in a Bi38-3 dose dependent manner, with a half maximal effective concentration ($EC_{50}$) around 5 ng/mL, the equivalent of 0.09 nM for this 55.6 Kd protein (data not shown). Bi38-3 mediated T cell cytotoxic activity was also observed in co-culture with MM1.S cells. However, in this cell line, which expresses higher levels of CD38, the $EC_{50}$ was tenfold lower (0.5 ng/mL), indicating a stronger efficiency of Bi38-3. In contrast, the viability of MM1.S or KMS11 MM cells was not affected by co-culture with T cells or Bi38-3 alone (data not shown). Furthermore, Bi38-3 induced poor T cell-mediated killing of MM1.S-KO cells, with around half of CD38-deficient MM1.S cells surviving the co-culture even at the highest dose of Bi38-3 (1 μg/mL) data not shown). Thus, Bi38-3 directed efficient T-cell cytotoxic activity on CD38 expressing MM cells.

Bi38-3 Induces Autologous T-Cell Mediated Killing of Tumor Plasma Cells In Vitro We next analyzed the potential of Bi38-3 to induce lysis of MM cells by autologous T cells. Target tumor plasma cells, isolated from patients at diagnosis, were incubated with purified autologous effector T cells in a E:T 1:5 ratio in the presence of various concentrations of Bi38-3. FACS analysis of overnight co-cultures revealed that the numbers of viable CD138 positive MM cells were reduced in a Bi38-3 dose dependent manner, with the $EC_{50}$ ranging from 0.5 to 1 ng/mL, depending on the patient (FIG. 1). Importantly, in the absence of T cells, Bi38-3 exhibited no toxicity against fresh primary MM cells. Bi38-3 induced cytotoxicity of autologous T cells was further investigated on tumor plasma cells from MM patients at relapse and demonstrated similar efficacy, with $EC_{50}$ ranging from 0.2 to 1 ng/mL (FIG. 1). Thus, in these in vitro experiments, Bi38-3 triggered autologous T cell-mediated killing of tumor plasma cells from patients both at diagnosis and at relapse.

Specific Activity of Bi38-3 Against CD38 Highly Expressing MM Cells In Vitro

While CD38 is highly expressed on plasma cells, it is also expressed on various cell types, including subsets of hematopoietic cells. To investigate the effect of Bi38-3 on blood cells, PBMC from donors were treated with various concentrations of Bi38-3 for 24 hours and the different cells populations were analyzed by FACS (data not shown). We observed that the percentages of CD14 expressing monocytes falling in the live gate were markedly reduced in a Bi38-3 dose dependent manner (data not shown). In contrast, the percentages of CD4 and CD8 T lymphocytes, that together represented around 60% of the PBMC population, slightly increased in response to Bi38-3 as the percentages of CD14 positive cells decreased. Similarly, the B (CD19+) and NK (CD56+) cell populations slightly raised or remained at similar levels (around 10% and 5% respectively), even at high concentrations of Bi38-3 (100 ng/mL) (data not shown). Next, we investigated whether expression of CD38 at the surface of blood cells was impaired by Bi38-3. FACS analysis indicated that CD38 Mean Intensity of fluorescence (MIF) on T, B and NK cells remained similar in cultures containing increasing doses of Bi38-3 (data not shown). In line with this, CD38 expression was not dramatically reduced on CD14+ myeloid cells, although because no or too few cells could be detected, analysis could not be performed at higher doses of Bi38-3 (1 and 100 ng/mL). To compare the activity of Bi38-3 on CD38 high (CD38hi) MM versus CD38 intermediate (CD38int) cells, we performed co-culture assays with MM1.S, expressing high levels of CD38 (data not shown), freshly isolated B cells, expressing intermediate amount of CD38 (data not shown) and autologous T cells. Following an overnight culture, the percentages of viable CD20 positive B cells and CD138 positive MM1.S cells were analyzed by flow cytometry. We observed that the percentages of MM1.S cells dropped at Bi38-3 concentrations of 0.1 ng/mL and this reduction was more dramatic at higher doses (data not shown). In contrast, compared to untreated conditions, the percentages of viable CD20-positive B cells remained unchanged even at high concentrations of Bi38-3 (data not shown).

We developed a similar autologous tri-culture assay to investigate potential toxic effects of Bi38-3 on CD34+ bone marrow hematopoietic progenitors and on regulatory T cells (Treg), which both express low levels of CD38. While Bi38-3 readily induced MM cell killing at low concentrations (10-2 ng/mL and above), we found that it triggered no significant T cell mediated cytotoxicity on Foxp3+ Treg (FIG. 2A). Similarly, there was no significant toxicity on CD34+ hematopoietic progenitors at concentrations below 10 ng/mL and moderate toxicity (>40% survival) at the highest concentrations (FIG. 2B). Altogether, our results indicate that Bi38-3 does not impair the surface expression of CD38 and only triggers T cell mediated killing of cells expressing high levels of CD38 with no or limited toxicity against cells expressing intermediate levels of CD38, such as hematopoietic progenitors, B, T or NK cells.

Altogether, our results indicate that Bi38-3 does not impair the surface expression of CD38 and triggers T cell mediated killing of CD38hi cells without significant activity against CD38int cells.

Bi38-3 Controls MM Cell Expansion In Vivo

The in vivo antitumor activity of Bi38-3 was assessed using a human MM xenograft mouse model. MM1.Sluc cells were injected in the tail vein of the NSG mice and luciferase levels measured by IVIS Imaging System every 4 days. Fourteen days after MM1.S injection, purified human T cells were transplanted I.V. with or without Bi38-3 (0.08 mg/kg). Treatments with Bi38-3 or vehicle were repeated daily for 7 days (FIG. 2A). Eleven days following tumor cell injection, all mice showed similar levels of Radiance (luciferase), indicating that MM cells had effectively engrafted in host animals prior to Bi38-3 treatment (FIG. 2B). While control mice showed rapid tumor progression, all Bi38-3 treated animals displayed a fivefold reduction in tumor growth within the first 4 days of Bi38-3 treatment (FIG. 2C). After 7 days, the level of luciferase expressing MM cells in Bi38-3 treated mice was only one tenth of the initial level and was fifty fold lower than untreated controls. These results indicate that Bi38-3 is efficient to control MM tumor progression in vivo.

Discussion:

We report here the development of Bi38-3, a new anti-CD38/CD3 Bispecific T cell-engager antibody, which triggers specific T-cell mediated lysis of CD38-positive MM cells in vitro, ex vivo and in vivo.

Monoclonal antibodies (Mab) targeting CD38 have shown therapeutic efficiencies in the treatment of MM[13]. Daratumumab, an anti-CD38 Mab approved for MM, has shown good therapeutic efficacy, both alone[14] or in combination with normal standard of care regimens[2,15]. These clinical data demonstrate that CD38, which is highly expressed on tumor plasma cells, is a target of choice for immune therapies in MM. However, despite marked improved survival rates, many patients treated with Daratumumab eventually relapse because of resistance mechanisms, including FcγR dependent down regulation of CD38 on tumor cells as well as inhibition of complement dependent cytotoxicity, antibody-dependent cell mediated cytotoxicity and antibody dependent cellular phagocytosis[16]. Bi38-3 lacks the Fc region found on natural immunoglobulins, and recruits cytotoxic T cells through its anti-CD3 scFv without downregulating CD38 expression on target cells (data not shown). Thus, the Bi38-3-mediated T cell killing of MM cells will not be affected by the mechanisms of resistance to anti-CD38 mAbs such as Daratumumab, which are associated with binding of the therapeutic antibody to FcγR. Similarly, up regulation of complement inhibitors CD55 and CD59 on cytotoxic cells, that are observed at relapse[17] and are thought to contribute to resistances, should not occur upon Bi38-3 treatment. In addition, MM is characterized by a defective immune system, and standard of care regimens that associate IMIDs and dexamethasone potentially limit the effectiveness of cytotoxic cells. However, our data demonstrate that Bi38-3 mediates autologous T cell mediated killing of tumor plasma cell from patients at diagnosis and at relapse with similar efficiencies (FIG. 1). Together, these data suggest that Bi38-3 could efficiently eliminate MM cells in patients that are resistant to standard treatments, including those that include Daratumumab.

Because CD38 is expressed at the surface of blood cells, including T, B and NK lymphocytes[18], anti-CD38 mAb may potentially target them and impair their functions. Indeed, Daratumumab was shown to eliminate regulatory T cells[19], a process which could be associated with increased T cell numbers and activation during the initiation phase of the treatment[16]. Furthermore, Daratumumab treatment results in the depletion of NK cells[20] and could favor the susceptibility of patients to infections[21]. Our data show that Bi38-3 has no significant effect on T, B and NK cells in vitro (data not shown). We also report that, even at high doses (10 ng/mL), it readily induced T cell mediated killing of MM cells, while preserving B cells from T cell cytotoxic activity. Interestingly, these results contrast with the activity of AMG424, a recently described anti-CD38 BiTEs, which triggered T cell cytotoxicity on B, T and NK cells in vitro[22]. Although additional experiments are required to evaluate the toxicity of Bi38-3 in in vivo models, in particular against myeloid cells, our results suggest that Bi38-3 could efficiently induce elimination of MM cells without impacting cells expressing low levels of CD38.

Recently, bispecific antibodies directed against the Fc receptor-like 5 (Fcrl5 or FcHR5) or the B-cell maturation antigen (BCMA) have been reported[10,12,23]. BI 836909, a BiTE targeting BCMA and CD3ε was shown to eliminate MM cells in a NCI-H929 mouse xenograft model at a dose of 0.5 mg/Kg[23]. Similarly, EM801, an asymmetric bispecific antibody containing a mutated Fc region, efficiently eliminated NCI-H929 cells in immunocompromised mice at the same dose (0.5 mg/Kg)[10]. Expression of BCMA is restricted to post germinal B cells, including memory B cells and both normal and malignant plasma cells[24]. However, although the majority of MM patients express BCMA, 6-9% of cases are negative for this marker and expression levels on tumor plasma cells is heterogeneous among patients[25,26]. Furthermore, in MM patients treated with T cells expressing anti-BCMA chimeric antigen receptors, BCMA is downregulated on tumor plasma cells[27], a process that could contribute to tumor escape and relapse. Altogether, these data emphasize the needs to identify and evaluate additional targets in MM. Indeed the development of efficient and safer bi-specific antibody could contribute to improve the treatment of MM.

Our data demonstrate that targeting CD38 with Bi38-3 is efficient in a xenograft model at 0.1 mg/Kg (FIG. 2), a dose significantly lower than the one reported for BCMA bispecific antibodies in similar mouse models[10,23]. Thus, Bi-38-3 may represent an attractive therapeutic option in MM cases expressing no or very low BCMA levels.

Although BiTEs have proven their efficacy in several malignancies, their clinical development is hampered by short half-life in patients, requiring continuous infusion via a pump[9]. The CD19/CD3 BiTE Blinatumomab was recently approved for treatment of minimal residual disease (MRD) in acute lymphoblastic leukemia (ALL). Interestingly, early phase 2 clinical trials demonstrated that the MRD negativity, which is associated with improved survival, may occur at the end of the first cycle of treatment[28,29]. While the optimal number of cycles of blinatumomab in the setting of MRD remains to be further studied in ALL, the clinical data demonstrate that limited BiTEs treatments over time may still improve the outcomes of MRD+ patients. In our study, we show that Bi38-3 was able to trigger a six-fold reduction in tumor burden in only 3 days in vivo, despite the use of a highly proliferating MM cell line (MM1.S) (FIG. 2C). Thus, this rapid and pronounced activity on tumor plasma cells suggests that, as with blinatumomab in ALL, Bi38-3 could eliminate MRD in MM patients after limited numbers of cycles and improve outcomes following standard treatments.

In summary, the data presented in this manuscript identify Bi38-3 as a selective and efficient compound in the treatment of MM, that could be used both front line or at relapse, and support further evaluation in MM patients.

EXAMPLE 2: PRODUCTION OF CAR-T CELLS

Methods:
Production of Transduced CAR-T Cells

HEK293 cells were calcium phosphate transfected with 10 μg CAR constructs and helper plasmids (psPAX2 and pMD2.G). Twelve hours post transfection, complete medium (DMEM, 10% FVS) was refreshed, and 2 days after transfection, cell-free supernatants containing retroviral particles were collected, concentrated by centrifugation and used for transduction. T cells (purified using Pan T-cell isolation kits from Miltenyi Biotec) were stimulated with CD3/CD28 beads (ThermoFisher) in culture medium (RPMI1640, 10% FBS, penicillin; 100 U/mL, streptomycin; 100 mg/mL). After 16 hours, cells were transferred to retronectin-coated (15 mg/mL) (Takara) 6-well plates (Falcon) and transduced over night with the indicated lentiviral particles. Seventy-two hours post transduction GFP and CAR expression were measured by flow cytometry to determine transduction efficiency. Transduced CAR-T cells represented more than 80% of total cells and were used for in vitro experiments.

Results:
Anti-CD38 CAR-T Cells Trigger MM Cell Lysis In Vitro

Since Bi38-3 induced T cells mediated lysis of MM cells (see EXAMPLE 1), we investigated whether its anti-CD38 scFv could trigger direct cytotocicity of transgenic T cells in the context of a chimeric antigen receptor (CAR). We developed a first generation anti-CD3 8 CAR construct (CAR CD38 1G) containing the BB51 derived anti-CD38 scFv, the hinge and transmembrane regions of human CD8 and the CD3ζ signaling domain (FIG. 3A). Because the association of the CD3ζ activation region with costimulatory signaling domains was shown to enhanced the activity of CARs, we also constructed a third generation anti-CD38 CAR (CAR CD38 3G) consisting of the anti-CD38 scFv, the CD28 transmembrane region and the signaling domains of CD28, CD137 (4-1BB) and CD3ζ, in that order (FIG. 3A). As controls, we generated a CAR devoid of scFv domain (CAR Mock) as well as a CAR of co-stimulation (CCR CD38) resembling the CD38 3G but lacking the CD3ζ signaling domain. The protein sequences corresponding to these constructs are depicted in Table 2. The DNA sequences encoding each CAR were cloned into a lentiviral vector allowing GFP co-expression, in order to produce viral particles and to transduce donor T cells. All CAR constructs were expressed upon transduction on human T lymphocytes (CAR-T), however, CAR CD38 3G was expressed at lower levels than the other constructs (data not shown). Despite this difference, all transduced T cells could be expanded over 2 weeks in vitro with stable expression of the CAR, indicating that potential fratricide effects on CD38 expressing T-cells still allowed CAR-T culture (data not shown). To investigate the cytotoxic function of effector CAR-T cells (E), we performed co-culture experiments with various ratios of luciferase expressing targets cells (T). CD38 expressing MM1.S and RPMI8288 MM cells were readily lysed by both CAR CD38 1G and 3G compared to Mock and CCR CD38 negative controls (FIG. 3B). Even at low E/T ratios (<2.5), anti-CD38 CAR-T killed MM cells, whereas CCR CD38 and Mock transduced T cells displayed poor cytotoxicity. In contrast, CAR CD38 1G and 3G induced no or very little lysis of CD38 negative HEK293 cells (FIG. 3B). Thus, the anti-CD38 scFv derived from the BB51 hybridoma is efficient to drive T-cell cytotoxicity on MINI cells in the context of different CAR constructs.

TABLE 2

Amino acid sequences of 1st and 3rd generation anti-CD38 CARs (CAR CD38 1G and 3G, respectively) and co-stimulation CAR (CCR CD38).

| | | |
|---|---|---|
| CAR CD38 1G | MALPVTALLLPLALLLHAARPDIQMTQSPASLSA<br>SVGETVTITCRASENIYSFLAWYQQKQGKSPQLL<br>VYNTKTLTEGVPSRFSGSGSGTQFSLKINNLQPE<br>DFGSYYCQHHYGIPLTFGAGTKLELKGGGGSGGG<br><br>GSGGGGSQVQLQQSGAELARPGASVKLSCKASGY<br>TFTSYWMQWVKQRPGQGLEWIGAIYPGDGDTRYT<br>QKFKGKATLTADKSSSTAYMQLSNLTSEDSAVYY<br>CARERTTGAPRYFDVWGAGTTVTVSSLEHFVPVF<br><br>LPAKPTTTPAPRPPTPAPTIASQPLSLRPEACRP<br><br>AAGGAVHTRGLDFACDIYIWAPLAGTCGVLLLSL<br><br>VITLYCNHRNRVKFSRSADAPAYQQGQNQLYNEL<br><br>NLGRREEYDVLDKRRGRDPEMGGKPQRRKNPQEG<br><br>LYNELQKDKMAEAYSEIGMKGERRRGKGHDGLYQ<br><br>GLSTATKDTYDALHMQALPPR-<br><br>(SEQ ID NO: 16) | Leader CD8a:<br>MALPVTALLLPLALLLHAARP<br>scFv anti CD38<br>Hinge and TM CD8 CD3ζ |

TABLE 2-continued

Amino acid sequences of 1ˢᵗ and 3ʳᵈ generation anti-CD38 CARs (CAR CD38 1G and 3G, respectively) and co-stimulation CAR (CCR CD38).

| | | |
|---|---|---|
| CAR CD38 3G | MALPVTALLLPLALLLHAARP*DIQMTQSPASLSA* <br> *SVEGETVTITCRASENIYSFLAWYQQKQGKSPQLL* <br> *VYNTKTLTEGVPSRFSGSGSGTQFSLKINNLQPE* <br> *DFGSYYCQHHYGIPLTFGAGTKLELKGGGGSGGG* | Leader CD8a: <br> MALPVTALLLPLALLLHAARP <br> scFv anti CD38 <br> Hinge, TM and intra CD28 |
| | *GSGGGGSQVQLQQSGAELARPGASVKLSCKASGY* | 4-1BB intra |
| | *TFTSYWMQWVKQRPGQGLEWIGAIYPGDGDTRYT* | CD3ζ |
| | *QKFKGKATLTADKSSSTAYMQLSNLTSEDSAVYY* <br> *CARERTTGAPRYFDVWGAGTTVTVSSLEIEVMYP* <br> PPYLDNEKSNGTIIHVKGKHLCPSPLFPGPSKPF <br> WVLVVVGGVLACYSLLVTVAFIIFWVRSKRSRLL <br> HSDYMNMTPRRPGPTRKHYQPYAPPRDFAAYRSK <br> RGRKKLLYIFKQPFMRPVQTTQEEDGCSCRFPEE <br> EEGGCELGSRVKFSRSADAPAYQQGQNQLYNELN <br> LGRREEYDVLDKRRGRDPEMGGKPRRKNPQEGLY <br> NELQKDKMAEAYSEIGMKGERRRGKGHDGLYQGL <br> STATKDTYDALHMQALPPR- | |
| | (SEQ ID NO: 17) | |
| CCR CD38 | *MALPVTALLLPLALLLHAARP*DIQMTQSPASLSA <br> SVEGETVTITCRASENTYSFLAWYQQKQGKSPQLL <br> VYNTKTLTEGVPSRFSGSGSGTQFSLKINNLQPE <br> DFGSYYCQHHYGIPLTFGAGTKLELKGGGGSGGG | Leader CD8a: <br> MALPVTALLLPLALLLHAARP <br> scFv anti CD38 <br> Hinge, TM and intra CD28 |
| | *GSGGGGSQVQLQQSGAELARPGASVKLSCKASGY* | 4-1BB intra |
| | *TFTSYWMQWVKQRPGQGLEWIGAIYPGDGDTRYT* <br> *QKFKGKATLTADKSSSTAYMQLSNLTSEDSAVYY* <br> *CARERTTGAPRYFDVWGAGTTVTVSSLEIEVMYP* <br> PPYLDNEKSNGTIIHVKGKHLCPSPLFPGPSKPF <br> WVLVVVGGVLACYSLLVTVAFIIFWVRSKRSRLL <br> HSDYMNMTPRRPGPTRKHYQPYAPPRDFAAYRSK <br> RGRKKLLYIFKQPFMRPVQTTQEEDGCSCRFPEE <br> EEGGCEL- | |
| | (SEQ ID NO: 18) | |

REFERENCES

Throughout this application, various references describe the state of the art to which this invention pertains. The disclosures of these references are hereby incorporated by reference into the present disclosure.

1. Dimopoulos, M. A., Richardson, P. G., Moreau, P. & Anderson, K. C. Current treatment landscape for relapsed and/or refractory multiple myeloma. Nat Rev Clin Oncol 12, 42-54, doi:10.1038/nrclinonc.2014.200 (2015).
2. Dimopoulos, M. A. et al. Daratumumab, Lenalidomide, and Dexamethasone for Multiple Myeloma. N Engl J Med 375, 1319-1331, doi:10.1056/NEJMoa1607751 (2016).
3. Facon, T. et al. Daratumumab plus Lenalidomide and Dexamethasone for Untreated Myeloma. N Engl J Med 380, 2104-2115, doi:10.1056/NEJMoa1817249 (2019).
4. Moreau, P. et al. Bortezomib, thalidomide, and dexamethasone with or without daratumumab before and after autologous stem-cell transplantation for newly diagnosed multiple myeloma (CASSIOPEIA): a randomised, open-label, phase 3 study. Lancet, doi:10.1016/S0140-6736(19) 31240-1 (2019).
5. Bannas, P., Hambach, J. & Koch-Nolte, F. Nanobodies and Nanobody-Based Human Heavy Chain Antibodies As Antitumor Therapeutics. Front Immunol 8, 1603, doi: 10.3389/fimmu.2017.01603 (2017).
6. Brischwein, K. et al. MT110: a novel bispecific single-chain antibody construct with high efficacy in eradicating established tumors. Mol Immunol 43, 1129-1143, doi: 10.1016/j.molimm.2005.07.034 (2006).
7. Foster, J. B. & Maude, S. L. New developments in immunotherapy for pediatric leukemia. Curr Opin Pediatr 30, 25-29, doi:10.1097/MOP.0000000000000572 (2018).
8. Zimmerman, Z., Maniar, T. & Nagorsen, D. Unleashing the clinical power of T cells: CD19/CD3 bi-specific T cell engager (BiTE®) antibody construct blinatumomab as a potential therapy. Int Immunol 27, 31-37, doi:10.1093/intimm/dxu089 (2015).

9. Velasquez, M. P., Bonifant, C. L. & Gottschalk, S. Redirecting T cells to hematological malignancies with bispecific antibodies. Blood 131, 30-38, doi:10.1182/blood-2017-06-741058 (2018).
10. Seckinger, A. et al. Target Expression, Generation, Preclinical Activity, and Pharmacokinetics of the BCMA-T Cell Bispecific Antibody EM801 for Multiple Myeloma Treatment. Cancer Cell 31, 396-410, doi:10.1016/j.ccell.2017.02.002 (2017).
11. Hipp, S. et al. A novel BCMA/CD3 bispecific T-cell engager for the treatment of multiple myeloma induces selective lysis in vitro and in vivo. Leukemia 31, 1743-1751, doi:10.1038/leu.2016.388 (2017).
12. Li, J. et al. Membrane-Proximal Epitope Facilitates Efficient T Cell Synapse Formation by Anti-FcRH5/CD3 and Is a Requirement for Myeloma Cell Killing. Cancer Cell 31, 383-395, doi:10.1016/j.ccell.2017.02.001 (2017).
13. van de Donk, N., Richardson, P. G. & Malavasi, F. CD38 antibodies in multiple myeloma: back to the future. Blood 131, 13-29, doi:10.1182/blood-2017-06-740944 (2018).
14. Usmani, S. Z. et al. Clinical efficacy of daratumumab monotherapy in patients with heavily pretreated relapsed or refractory multiple myeloma. Blood 128, 37-44, doi:10.1182/blood-2016-03-705210 (2016).
15. Palumbo, A. et al. Daratumumab, Bortezomib, and Dexamethasone for Multiple Myeloma. N Engl J Med 375, 754-766, doi:10.1056/NEJMoa1606038 (2016).
16. van de Donk, N. & Usmani, S. Z. CD38 Antibodies in Multiple Myeloma: Mechanisms of Action and Modes of Resistance. Front Immunol 9, 2134, doi:10.3389/fimmu.2018.02134 (2018).
17. Nijhof, I. S. et al. CD38 expression and complement inhibitors affect response and resistance to daratumumab therapy in myeloma. Blood 128, 959-970, doi:10.1182/blood-2016-03-703439 (2016).
18. Deaglio, S., Aydin, S., Vaisitti, T., Bergui, L. & Malavasi, F. CD38 at the junction between prognostic marker and therapeutic target. Trends Mol Med 14, 210-218, doi:10.1016/j.molmed.2008.02.005 (2008).
19. Krejcik, J. et al. Daratumumab depletes CD38+ immune regulatory cells, promotes T-cell expansion, and skews T-cell repertoire in multiple myeloma. Blood 128, 384-394, doi:10.1182/blood-2015-12-687749 (2016).
20. Casneuf, T. et al. Effects of daratumumab on natural killer cells and impact on clinical outcomes in relapsed or refractory multiple myeloma. Blood Adv 1, 2105-2114, doi:10.1182/bloodadvances.2017006866 (2017).
21. Nahi, H. et al. Infectious complications and NK cell depletion following daratumumab treatment of Multiple Myeloma. PLoS One 14, e0211927, doi:10.1371/journal.pone.0211927 (2019).
22. Zuch de Zafra, C. L. et al. Targeting Multiple Myeloma with AMG 424, a Novel Anti-CD38/CD3 Bispecific T-cell-recruiting Antibody Optimized for Cytotoxicity and Cytokine Release. Clin Cancer Res, doi:10.1158/1078-0432.CCR-18-2752 (2019).
23. Hipp, S. et al. A novel BCMA/CD3 bispecific T-cell engager for the treatment of multiple myeloma induces selective lysis in vitro and in vivo. Leukemia 31, 2278, doi:10.1038/leu.2017.219 (2017).
24. Darce, J. R., Arendt, B. K., Wu, X. & Jelinek, D. F. Regulated expression of BAFF-binding receptors during human B cell differentiation. J Immunol 179, 7276-7286, doi: 10.4049/jimmunol.179.11.7276 (2007).
25. Lee, L. et al. Evaluation of B cell maturation antigen as a target for antibody drug conjugate mediated cytotoxicity in multiple myeloma. Br J Haematol 174, 911-922, doi: 10.1111/bjh.14145 (2016).
26. Salem, D. A. et al. Quantification of B-cell maturation antigen, a target for novel chimeric antigen receptor T-cell therapy in Myeloma. Leuk Res 71, 106-111, doi:10.1016/j.leukres.2018.07.015 (2018).
27. Brudno, J. N. et al. T Cells Genetically Modified to Express an Anti-B-Cell Maturation Antigen Chimeric Antigen Receptor Cause Remissions of Poor-Prognosis Relapsed Multiple Myeloma. J Clin Oncol 36, 2267-2280, doi:10.1200/JCO.2018.77.8084 (2018).
28. Gokbuget, N. et al. Blinatumomab for minimal residual disease in adults with B-cell precursor acute lymphoblastic leukemia. Blood 131, 1522-1531, doi:10.1182/blood-2017-08-798322 (2018).
29. Topp, M. S. et al. Targeted therapy with the T-cell-engaging antibody blinatumomab of chemotherapy-refractory minimal residual disease in B-lineage acute lymphoblastic leukemia patients results in high response rate and prolonged leukemia-free survival. J Clin Oncol 29, 2493-2498, doi:10.1200/JCO.2010.32.7270 (2011).

---

The invention claimed is:

1. A monoclonal antibody having binding specificity for the extracellular domain of CD38 which comprises:
   a heavy chain comprising i) the H-CDR1 as set forth in SEQ ID NO:5, ii) the H-CDR2 as set forth in SEQ ID NO:6 and iii) the H-CDR3 as set forth in SEQ ID NO:7, and,
   a light chain comprising i) the L-CDR1 as set forth in SEQ ID NO:8, ii) the L-CDR2 as set forth in SEQ ID NO:9 and iii) the L-CDR3 as set forth in SEQ ID NO:10.

2. The monoclonal antibody of claim 1 which comprises a VH domain having at least 70% of identity with the amino acid sequence as set forth in SEQ ID NO: 3.

3. The monoclonal antibody of claim 1 which comprises a VL domain having at least 70% of identity with the amino acid sequence as set forth in SEQ ID NO:4.

4. The monoclonal antibody of claim 1 which is a chimeric antibody.

5. The monoclonal antibody of claim 1 which is a humanized antibody.

6. A scFv fragment comprising the VH and the VL domain of the antibody of claim 1.

7. The scFv fragment of claim 6 which has an amino acid sequence as set forth in SEQ ID NO:11.

8. A multispecific antibody comprising a first antigen binding site from the monoclonal antibody of claim 1 and at least one second antigen binding site.

9. A The multispecific antibody of claim 8 wherein the second antigen binding site is used for recruiting T cells.

10. The multispecific antibody of claim 9 wherein the second antigen binding site has specificity for the extracellular domain of CD38.

11. The multispecific antibody of claim 8 which comprises an antigen-binding domain comprising the single chain variable fragment (scFv) of claim 6.

12. The multispecific antibody of 8 which comprises the sequence as set forth in SEQ IQ NO: 12.

13. A chimeric antigen receptor (CAR) comprising an antigen binding domain of the antibody of claim 1.

14. The chimeric antigen receptor (CAR) of claim 13 comprising an antigen-binding domain comprising the single chain variable fragment (scFv) of claim 6.

15. The chimeric antigen receptor (CAR) of claim 14 which comprises an extracellular hinge domain, a transmembrane domain, and an intracellular T cell signaling domain selected from the group consisting of CD28, 4-1BB, and CD3 intracellular domains.

16. The chimeric antigen receptor (CAR) of claim 14 which has an amino acid sequence as set forth in SEQ ID NO: 13 or 14.

17. A nucleic acid sequence encoding i) the monoclonal antibody of claim 1, ii) a multispecific antibody comprising a first antigen binding site from the monoclonal antibody and at least one second antigen binding site, or iii) a chimeric antigen receptor (CAR) comprising an antigen binding domain of the monoclonal antibody.

18. A nucleic acid sequence which encodes a heavy chain and/or a light chain of the monoclonal antibody of claim 1.

19. A vector comprising the nucleic acid of claim 17.

20. A host cell engineered to express i) the monoclonal antibody of claim 1, ii) a multispecific antibody comprising a first antigen binding site from the monoclonal antibody and at least one second antigen binding site, or iii) a chimeric antigen receptor (CAR) comprising an antigen binding domain of the monoclonal antibody.

21. The host cell of claim 20 which is a CAR-T cell.

22. A method of treating cancer in a patient in need comprising administering to the subject a therapeutically effective amount of i) the antibody of claim 1 and/or ii) a multispecific antibody comprising a first antigen binding site from the monoclonal antibody and at least one second antigen binding site and/or iii) a population of CAR-T cells of engineered to express the monoclonal antibody or a multispecific antibody comprising a first antigen binding site from the monoclonal antibody or a chimeric antigen receptor (CAR) comprising an antigen binding domain of the monoclonal antibody.

23. A pharmaceutical composition comprising an amount of i) the antibody of claim 1 and/or ii) a multispecific antibody comprising a first antigen binding site from the monoclonal antibody and at least one second antigen binding site and/or ii) the population of CAR-T cells of engineered to express the monoclonal antibody or a multispecific antibody comprising a first antigen binding site from the monoclonal antibody or a chimeric antigen receptor (CAR) comprising an antigen binding domain of the monoclonal antibody.

24. The monoclonal antibody of claim 4 wherein the chimeric antibody has a heavy chain as set forth in SEQ ID NO:3 and/or a light chain as set forth in SEQ ID NO: 4.

25. The method of claim 22, wherein the cancer is a CD38-positive hematological malignancy.

\* \* \* \* \*